US005883255A

United States Patent [19]
Berges et al.

[11] Patent Number: 5,883,255
[45] Date of Patent: *Mar. 16, 1999

[54] SUBSTITUTED INDOLIZINO[1,2-B] QUINOLINONES

[75] Inventors: David Alan Berges, Phoenixville; Robert Philip Hertzberg, Downingtown; Randall Keith Johnson, Ardmore; William Dennis Kingsbury, Wayne, all of Pa.

[73] Assignee: SmithKline Beecham Corporation, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 807,614

[22] Filed: Feb. 27, 1997

Related U.S. Application Data

[63] Continuation of Ser. No. 450,435, May 25, 1995, abandoned, which is a continuation of Ser. No. 48,391, Apr. 14, 1993, which is a continuation-in-part of Ser. No. 870,649, Apr. 17, 1992, abandoned, which is a continuation of Ser. No. 783,063, Oct. 25, 1991, which is a continuation-in-part of Ser. No. 606,216, Oct. 31, 1990, abandoned.

[51] Int. Cl.$^6$ ................................................. C07D 273/00
[52] U.S. Cl. ............................................... 546/70; 514/285
[58] Field of Search ............................... 546/70; 514/285

[56] References Cited

U.S. PATENT DOCUMENTS

| | | | |
|---|---|---|---|
| 4,473,692 | 9/1984 | Miyasaka et al. | 491/147 |
| 4,894,456 | 1/1990 | Wall et al. | 31/47 |
| 4,914,205 | 4/1990 | Sawada et al. | 546/70 |
| 4,943,579 | 7/1990 | Vishnuvajjala et al. | 514/283 |
| 4,981,968 | 1/1991 | Wall et al. | 544/361 |
| 5,061,800 | 10/1991 | Yaegashi et al. | 546/48 |
| 5,155,225 | 10/1992 | Fortunak et al. | 546/70 |
| 5,255,404 | 10/1993 | Giovannella et al. | 514/81 |
| 5,342,947 | 8/1994 | Lackey et al. | 546/41 |
| 5,405,963 | 4/1995 | Fortunak et al. | 546/48 |
| 5,468,859 | 11/1995 | Fortunak et al. | 546/48 |

FOREIGN PATENT DOCUMENTS

| | | |
|---|---|---|
| 0 321 122 A2 | 6/1989 | European Pat. Off. . |
| 49-117499 | 11/1974 | Japan . |
| 4-139188 | 8/1976 | Japan . |
| 51-91297 | 8/1976 | Japan . |
| 59-5188 | 1/1984 | Japan . |
| 59-46284 | 3/1984 | Japan . |
| 59-51 289 | 3/1984 | Japan . |
| WO 91/16904 | 11/1991 | WIPO . |
| WO 92/07856 | 5/1992 | WIPO . |
| WO 93/20818 | 10/1993 | WIPO . |
| WO 94/25465 | 11/1994 | WIPO . |

OTHER PUBLICATIONS

J.A. Adamovics, J.A. Cina and C.R. Hutchinson, Phytochemistry 1979, vol. 18, pp. 1085–1086, Aug. 1979.

T. Kametani, H. Takeda, H. Nemoto, K. Fukumoto, Journal of the Chemical Society, Perkin Transactions I, 1975, pp. 1825–1828, Apr. 1975.

T.R. Govindachari, K.R. Ravindrath, N. Viswanathan, Journal of the Chemical Society, Perkin Transactions I, 1974, pp. 1215–1217, Mar. 1974.

Kingsbury, "The Chemical Rearrangement of camptothecin to Mappicine Ketone", (1988), Tetrahedron Letters, 29(52), pp. 6847–6850.

Horwitz, et al., "Camptothecin: Mechanism of Inhibition of Adenovirus Formation[1]", (1972), Virology, 48, pp. 690–698.

Atherton, et al., "Interferon Induction of Viruses and Polynucleotides: A Differential Effect of Camptothecin", (1975), J. Gen. Virology, 29, pp. 297–304.

Chemical Abstracts No. 87:23591d, (1977), 87, p. 684.
Chemical Abstracts No. 85:177759k, (1976), 85,p. 558.
Chemical Abstracts No. 82:156550h, (1975), 82,p. 637.
Chemical Abstracts No. 84:5223u, (1976), 84,p. 447.
Chemical Abstracts No. 81:136341s, (1974), 81,p. 443.
Horwitz, Chem. Abstracts, Abstract No. 77:70781u, p. 7079.

Wall, et al., "Plant Antitumor Agents. I. The Isolation and Structure of Camptothecin, a Novel Alkaloidal Leukemia and Tumor Inhibitor from Camptotheca acuminata [1,2]", (1960), Jour. Amer. Chem. Soc., 88(16), pp. 3888–3890.

Wani, et al., "Plant Antitumor Agents. 23.[1] Synthesis and Antileukemic Activity of Camptothecin Analogues", (1986), J. Med. Chem., 29, pp. 2358–2363.

Wani, et al., "Plant Antitumor Agents. 25.[1] Total Synthesis and Antileukemic Activity of Ring A Substituted Camptothecin Analogues. Structure–Activity Correlations", (1987), J. Med. Chem., 30, pp. 1774–1779.

Govindachari, et al., "Mappicine, a Minor Alkaloid from *Mappia foetida* Miers", (1974), J.C.S. Perkins, pp. 1215–1217.

Kametani, et al., "Studies on the Syntheses of Heterocyclic Compounds. Part DCXXII.+Total Synthesis of . . ." (1975), J. Chem. Society, Perkins Translations I, pp. 1825–1828.

Adamovics, et al., "Minor Alkaloids of *Camptotheca Acuminata* " (1979), Phytochemistry, 18, pp. 1085–1086.

U.S. application No. 08/932,579, Kingsbury, et al., filed Sep. 19, 1997.

*Primary Examiner*—Charles Jordan
*Assistant Examiner*—John R. Hardee
*Attorney, Agent, or Firm*—Yuriy P. Stercho; Stephen A. Venetianer; Charles M. Kinzig

[57] ABSTRACT

The present invention provides a method of treating viral infections by using antiviral substituted indolizino[1,2-b] quinolinone compounds, antiviral substituted indolizino[1,2-b]quinolinone compounds, and pharmaceutical compositions thereof.

28 Claims, No Drawings

SUBSTITUTED INDOLIZINO[1,2-B] QUINOLINONES

This application is a continuation of Ser. No. 08/450,435, filed on May 25, 1995, now abandoned, which is a continuation of Ser. No. 08/048,391, filed on Apr. 14, 1993, which is a continuation-in-part of U.S. Ser. No. 07/870,649, filed on Apr. 17, 1992, now abandoned, which is a continuation of U.S. Ser. No. 07/783,063, filed on Oct. 25, 1991, which is a continuation-in-part of U.S. Ser. No. 07/606,216, filed on Oct. 31, 1990, now abandoned.

SCOPE OF THE INVENTION

This invention relates to methods of treating viral infections, antiviral compounds, and pharmaceutical compositions thereof. More specifically, this invention relates to a method of treating viral infections, certain indolizino[1,2-b]quinolinyl derivatives which have antiviral activity and pharmaceutical compositions thereof.

BACKGROUND

Certain 1H-pyrano[3',4':6,7]indolizino[1,2-b]quinolinones are known to have cytotoxic and antiviral activity. Camptothecin is an example of such compounds. It is a water-insoluble, cytotoxic alkaloid produced by *Camptotheca acuminata* trees indigenous to China and *Nothapodytes foetida* trees indigenous to India. Camptothecin and its close congeners are known to inhibit eukaryotic topoisomerase I. In fact, the cytotoxic and antitumor activity of camptothecin and its close congeners results from inhibition of eukaryotic topoisomerase I (*Cancer Res.* 1988, 48, 1722; *Molec. Pharmacol.* 1988, 34, 755). Compounds that are related in structure to camptothecin but do not inhibit eukaryotic topoisomerase I are not cytotoxic to mammalian cells and have no antitumor activity (*J. Med. Chem.* 1988, 32, 715; *Cancer Res.* 1989, 49, 1465; *Cancer Res.* 1989, 49, 4358).

A number of investigators have shown that camptothecin possesses antiviral activity. However, although camptothecin has demonstrated antiviral activity in in vitro tissue culture systems, camptothecin and its close analogs that have a hydroxylactone moiety cannot be considered as useful in vivo antiviral agents because they undesirably inhibit mammalian topoisomerase I, as well as host cell DNA replication, and are cytotoxic to mammalian cells. Furthermore, camptothecin is not an attractive candidate for drug development as an antiviral agent because of unacceptable dose-limiting toxicity, unpredictable toxicity, and poor aqueous solubility, and/or unacceptable shelf life stability.

There is a need for new antiviral agents. Substituted indolizino[1,2-b]quinolinones that lack the a-hydroxylactone moiety of camptothecin have been shown to be non-cytotoxic to mammalian cells and to lack antitumor activity (*Ann. Rev. Pharmcol. Toxicol.* 1977, 17, 117; *J. Med. Chem.* 1989, 32, 715). This is because these compounds do not contain the essential structural features required to inhibit eukaryotic topoisomerase I. However, recently we have found that certain substituted indolizino [1,2-b]quinolinones lacking the a-hydroxylactone moiety do have antiviral activity but not the undesirable cytotoxicity of camptothecin. Thus, such substituted indolizino[1,2-b] quinolinones are useful for treating viral infections.

SUMMARY OF THE INVENTION

One aspect of the present invention provides a method for treating viral infections comprising administering to an infected host in need thereof an effective amount of a compound of Formula I, or a pharmaceutically acceptable salt thereof, alone or in combination with a carrier

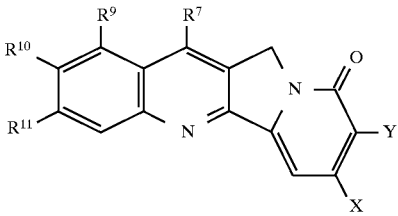

wherein:

$R^7$ is —H, —CN, lower alkyl or —$(CH_2)_nCH_2V$ where n=0–3;

$R^9$ is —H, —OR, —$NRR^1$, —CN, —$(CH_2)_nCH_2V$ where n=0–3;

$R^{10}$ is —H, —OR, —$NRR^1$, —CN, —$COR^{12}$, —CH$(OH)R^{12}$, —O—$(CH_2)_{1-5}CH_2NRR^1$, —OC(O)$NRR^1$, 1,4'-bipiperidine-1'-carboxy, —$(CH_2)_nCH_2V$ where n=0–3;

V is —OH, —$OCOR^{14}OP(O)(OH)R^{15}$ or —$NRR^1$;

$R^{11}$ is —H or —OR;

$R^{12}$ is —H or lower alkyl;

$R^{13}$ is lower alkyl;

R and $R^1$ are independently selected from the group consisting of —H, —$C_{1-6}$ alkyl, and, when R and $R^1$ are substituted on nitrogen, R and $R^1$ can be taken together to form a 5–7 membered saturated heterocyclic ring containing the nitrogen;

$R^{14}$ is —$CR^{12}R^{16}R^{17}$;

—$(CH_2)_nCH_2R^{17}$ (where n=1–3);

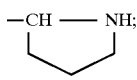

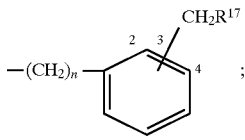

(where n=0 or 1, and $CH_2R^{17}$ can be substituted on the phenyl at the 2,3, or 4 position);

—$O(CH_2)_nCH_2R^{17}$ (where n=1–3);

—$NRR^1$;

—$NH(CH_2)_nCH_2R^{17}$ (where n=1–3);

$R^{15}$ is OH, $OR^{18}$ or $CH_2NH_2$;

$R^{16}$ is H or the side chain of any naturally occuring a-amino acid;

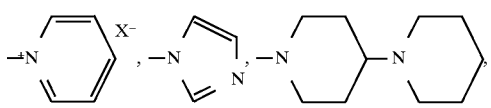

$R^{17}$ is $NRR^1$, where X is any pharmaceutically acceptable anion;

$R^{18}$ is lower alkyl;

X is —CH(OH)CH(OH)CH$_3$, —CHR$^3$R$^4$ or

Y is —CH$_3$ or —CH$_2$OR$^2$;
R$^2$ is —H, —C(O)H, —COR$^{14}$, or —P(O)(OH)R$^{15}$;
R$^3$ is —OH, —OCOR$^{14}$, or —OP(O)(OH)R$^{15}$;
R$^4$ is —H, lower alkyl, or —OR; and
R$^6$ is —H or lower alkyl.
provided that:
a) if one of R$^7$, R$^9$, R$^{10}$ or R$^{11}$ is other than —H, only one of the others may be other than —H;
b) only one of R$^9$ or R$^{10}$ may be —NRR$^1$;
c) when X is —CHR$^3$R$^4$ and R$^4$ is —OR, R$^3$ is —OH;
d) when Y is —CH$_2$OR$^2$, X is

This invention also provides compounds having the formula of Formula I as described hereinabove, except that:
a) when R$^7$, R$^9$, R$^{10}$, and R$^{11}$ are all —H and Y is —CH$_3$, then X is not —C(O)H, —CH$_2$OH, —C(O)CH$_2$CH$^3$, or —CH(OH)CH$_2$CH$_3$; and
b) when R$^7$, R$^9$, R$^{10}$ and R$^{11}$ are all —H and Y is —CH$_2$OC(O)H, then X is not —C(O)CH$_2$CH$_3$.

Another aspect of the present invention relates to pharmaceutical compositions comprising a compound of Formula I in combination with a pharmaceutically acceptable carrier or excipient.

In yet another aspect, the present invention relates to processes for making a compound of Formula I.

DETAILED DESCRIPTION OF THE INVENTION

The following definitions are used throughout this patent application.

"Aliphatic" is intended to include saturated and unsaturated radicals. This includes normal and branched chains, saturated or mono or poly unsaturated chains where both double and triple bonds may be present in any combination. The phrase "lower alkyl" and "C$_{1-6}$ alkyl" refer to an alkyl group of 1 to 6 carbon atoms in any isomeric form, but particularly the normal or linear form. "Lower alkoxy" means the group lower alkyl-O—. "Halo" means fluoro, chloro, bromo or iodo. "Acyl" means the radical having a terminal carbonyl carbon.

The phrase "5–7 membered saturated heterocyclic ring containing the nitrogen" is intended to include saturated rings such as piperidine, pyrrolidine, morpholine, piperazine, and N-alkyl piperazine.

The term "1,4'-bipiperidine-1'-carboxy" is used to identify the following radical:

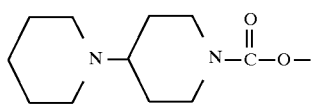

Salts of any sort may be made from these compounds, provided that an acidic group or a sufficiently basic nitrogen is present in the compound. Particularly preferred are the pharmaceutically acceptable salts of the instant compounds. These salts are defined as those which are acceptable in their application to a pharmaceutical use, meaning that the salt will retain the biological activity of the parent compound and that the salt will not have untoward or deleterious effects in its application and use in treating diseases.

Pharmaceutically acceptable salts are prepared in a standard manner. The parent compound, in a suitable solvent, is reacted with an excess of an organic or inorganic acid in the case of acid addition salts of a base moiety; or an excess of organic or inorganic base in the case where the parent contains an acid group. Representative acids are hydrochloric acid, hydrobromic acid, sulfuric acid, phosphoric acid, acetic acid, maleic acid, succinic acid and methanesulfonic acid. Cationic salts are readily prepared from alkali metals such as sodium, potassium, calcium, magnesium, zinc, copper or the like as well as ammonia. Organic bases include the mono or disubstituted amines, ethylenediamine, piperazine, amino acids, caffeine, and the like.

The chemical nomenclature used throughout this patent application to name the compounds of the present invention is in accordance with the structural formula represented as Formula II.

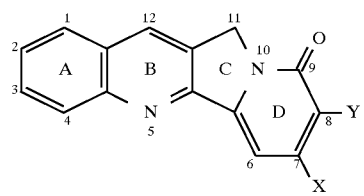

In the event that some combination of substituents creates a chiral center or another form of an isomeric center in a compound of this invention, all forms of such isomer(s) are considered to be aspects of the present inventions. When a compound of the present invention contains a chiral center, the present invention includes the racemic mixture, the pure enantiomers, and any enantiomerically enriched mixture thereof.

The present invention provides a method of treating viral infections comprising administering to an infected host in need thereof an effective amount of a compound of Formula I as described hereinabove, or a pharmaceutically acceptable salt thereof, alone or in combination with a carrier or excipient.

The present method is useful for treating viral infections in animals, particularly mammals, most particularly humans, caused by a broad variety of DNA replicating animal viruses. The present method is particularly useful in treating viral infections caused by herpes simplex virus, particularly herpes simplex virus type 1 (HSV1) and herpes simplex virus type 2 (HSV2), varicella zoster virus (VZV), or cytomegalovirus (CMV) when the infected host is a mammal, particularly when the infected host is human.

A preferred method of treating viral infections according to the present invention uses compounds of Formula IM1

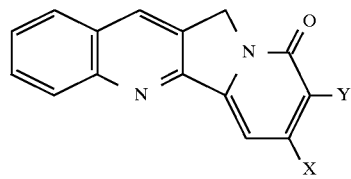

X is —CH(OH)CH(OH)CH₃, —CHR³R⁴, or

and Y is —CH₃ or —CH₂OR², Formula IM1 corresponding to Formula I wherein R⁷, R⁹, R¹⁰, and R¹¹ are each —H and X and Y are as described herein. A more preferred method uses compounds of Formula IM1 where X is CHR³R⁴ where R³ is —OH, OCOR¹⁴ or OP(O)(OH)R¹⁵ and Y is —CH₃, where X is

where R⁶ is —H or lower alkyl and Y is —CH₃ or —CH₂OR², or where X is —CH(OH)CH(OH)CH₃ and Y is —CH₃.

Another preferred method for treating viral infections according to the present invention uses compounds of Formula IM2

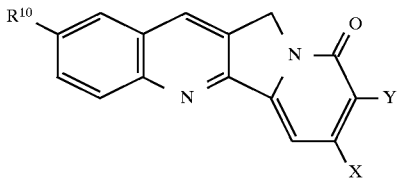

Formula IM2 corresponding to Formula I wherein R⁷, R⁹, and R¹¹ are each H, R¹⁰ is as defined hereinabove for Formula I except that R¹⁰ is not —H, and X and Y are as defined hereinabove in Formula I. A more preferred method uses compounds of Formula IM2 where R¹⁰ is —OR, —CN, COR¹², or —(CH₂)ₙCH₂V; or X is —CHR³R⁴ where R³ is —OH, OCOR¹⁴ or OP(O)(OH)R¹⁵ and R⁴ is —H or lower alkyl and Y is —CH₃, or X is

where R⁶ is —H or lower alkyl and Y is —CH₃ or CH₂OR².

Yet another preferred method of use according to the present invention uses compounds of Formula IM3

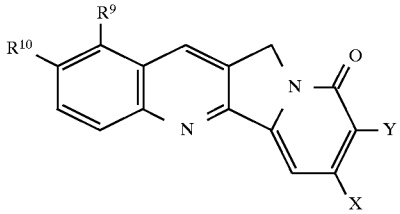

Formula IM3 corresponding to Formula I wherein R⁷ and R¹¹ are each —H, R⁹ and R¹⁰ are as defined hereinabove for Formula I except that R⁹ and R¹⁰ are each not —H, and X and Y are as defined hereinabove in Formula I. A more preferred method uses compounds of Formula IM3 wherein R⁹ is —(CH₂)ₙCH₂V, R¹⁰ is —OR, X is CHR³R⁴ where R³ is —OH, OCOR¹⁴ or OP(O)(OH)R¹⁵ and R⁴ is —H or lower alkyl, or X is

where R⁶ is —H or lower alkyl, and Y is —CH₃ or CH₂OR².

Another preferred method of use according to the present invention uses compounds of Formula IM4

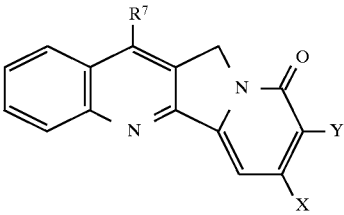

Formula IM4 corresponding to Formula I wherein R⁹, R¹⁰ and R¹¹ are each —H, R⁷ is as defined hereinabove except that R⁷ is not —H, and X and Y are as defined hereinabove in Formula I. A more preferred method uses compounds of Formula IM4 where R⁷ is lower alkyl, —CN, or —(CH₂)ₙCH₂V; X is CHR³R⁴ where R³ is —OH, OCOR¹⁴ or OP(O)(OH)R¹⁵ and R⁴ is —H or lower alkyl, or X is

where R⁶ is —H or lower alkyl, and Y is —CH₃ or CH₂OR².

Yet another preferred method of use according to the present invention uses compounds of Formula IM5

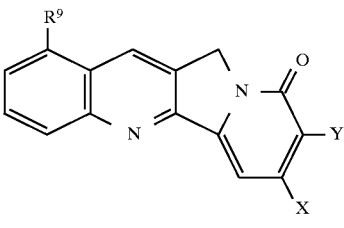

Formula IM5 corresponding to Formula I wherein R⁷, R¹⁰ and R¹¹ are —H, R⁹ is as defined hereinabove for Formula I except that R⁹ is not —H, and X and Y are as defined hereinabove in Formula I. A more preferred method uses compounds of Formula IM5 where R⁹ is —OR, X is CHR³R⁴ where R³ is —OH, OCOR¹⁴ or OP(O)(OH)R¹⁵ and R⁴ is —H or lower alkyl, or X is

where R⁶ is —H or lower alkyl, and Y is —CH₃ or CH₂OR².

Still another preferred method of use according to the present invention uses compounds is represented by Formula IM6

Formula IM6 corresponding to Formula I wherein $R^7$, $R^9$ and $R^{10}$ are each H, $R^{11}$ is —OR, and X and Y are as defined hereinabove in Formula I. A more preferred method uses compounds of Formula IM6 where $R^{11}$ is OR, X is $CHR^3R^4$ where $R^3$ is —OH, $OCOR^{14}$ or $OP(O)(OH)R^{15}$ and $R^4$ is —H or lower alkyl, or X is where $R^6$ is —H or lower alkyl, and Y is —$CH_3$ or $CH_2OR^2$.

The present invention also provides compounds having antiviral activity, and pharmaceutically acceptable salts thereof, said compound having the structure represented by Formula I hereinabove except that:

a) when $R^7$, $R^9$, $R^{10}$, and $R^{11}$ are all —H and Y is —$CH_3$, then X is not —C(O)H, —$CH_2OH$, —CH(OH)CH(OH)$CH_3$, —C(O)$CH_2CH_3$, or —CH(OH)$CH_2CH_3$; and b) when $R^7$, $R^9$, $R^{10}$ and $R^{11}$ are all —H and Y is —$CH_2OC(O)H$, then X is not —C(O)$CH_2CH_3$.

Preferred compounds of the present invention include those of Formula IN1

Formula IN1 corresponding to Formula I wherein $R^7$, $R^9$, $R^{10}$ and $R^{11}$ are each —H,
X is where $R^6$ is —H or lower alkyl, and Y is $CH_3$ or $CH_2OR^2$ (provided $R^6$ is not —$CH_2CH_3$ when Y is —$CH_3$) or X is $CHR^3R^4$ where $R^3$ is —OH, $OCOR^{14}$ or $OP(O)(OH)R^{15}$ and $R^4$ is —H or lower alkyl (provided that $R^4$ is not —$CH_2CH_3$ when $R^3$ is OH), and Y is —$CH_3$.

Compounds of Formula IN2 are also preferred according to the present invention

Formula IN2 corresponding to Formula I wherein $R^7$, $R^9$ and $R^{11}$ are each —H, $R^{10}$ is as described hereinabove for Formula I except that $R^{10}$ is not —H, and X and Y are as defined hereinabove for Formula I. More preferred compounds of Formula IN2 include those where $R^{10}$ is —OR, —CN, —$COR^{12}$, or —$(CH_2)_nCH_2V$, and X is $CHR^3R^4$ where $R^3$ is —OH, $OCOR^{14}$ or $OP(O)(OH)R^{15}$ and $R^4$ is —H or lower alkyl, or X is where $R^6$ is —H or lower alkyl, and Y is —$CH_3$ or $CH_2OR^2$.

Another preferred group of compounds of the present invention is represented by Formula IN3

Formula IN3 corresponding to Formula I wherein $R^7$ and $R^{11}$ are each —H, $R^9$ and $R^{10}$ are as described hereinabove for Formula I except that $R^9$ and $R^{10}$ are not —H, and X and Y are as defined hereinabove for Formula I. More preferred compounds of Formula IN3 include those where $R^9$ is —$(CH_2)_nCH_2V$, $R^{10}$ is —OR, X is $CHR^3R^4$ where $R^3$ is —OH, $OCOR^{14}$ or $OP(O)(OH)R^{15}$ and $R^4$ is —H or lower alkyl, or X is where $R^6$ is —H or lower alkyl, and Y is —$CH_3$ or $CH_2OR^2$.

Still another preferred group of inventive compounds is represented by Formula IN4

Formula IN4 corresponding to Formula I wherein $R^9$, $R^{10}$ and $R^{11}$ are each —H, $R^7$ is as described hereinabove for Formula I except that $R^7$ is not —H, and X and Y are as defined hereinabove for Formula I. More preferred compounds of Formula IN4 include those compounds where $R^7$ is lower alkyl, —CN, or —$(CH_2)_nCH_2V$; X is $CHR^3R^4$ where $R^3$ is —OH, $OCOR^{14}$ or $OP(O)(OH)R^{15}$ and $R^4$ is —H or lower alkyl, or X is where $R^6$ is —H or lower alkyl, and Y is —$CH_3$.

Another preferred group of compounds according to the present invention is represented by Formula IN5

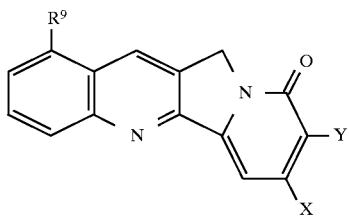

Formula IN5 corresponding to Formula I wherein $R^7$, $R^{10}$ and $R^{11}$ are each —H, $R^9$ is as described hereinabove for Formula I except that $R^9$ is not —H, and X and Y are as defined hereinabove for Formula I. More preferred compounds of Formula IN5 include those compounds where $R^9$ is —OR, X is $CHR^3R^4$ where $R^3$ is —OH, $OCOR^{14}$ or $OP(O)(OH)R^{15}$ and $R^4$ is —H or lower alkyl, or X is

where $R^6$ is —H or lower alkyl, and Y is —$CH_3$ or $CH_2OR^2$.

Yet a further group of preferred compounds is represented by Formula IN6

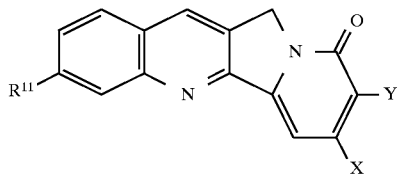

Formula IN6 corresponding to Formula I wherein $R^7$, $R^9$ and $R^{10}$ are each —H, $R^{11}$ is —OR, and X and Y are as defined hereinabove for Formula I. More preferred compounds of Formula IN6 are compounds where $R^{11}$ is —OR, X is $CHR^3R^4$ where $R^3$ is —OH, $OCOR^{14}$ or $OP(O)(OH)R^{15}$ and $R^4$ is —H or lower alkyl, or X is

where $R^6$ is —H or lower alkyl, and Y is —$CH_3$ or $CH_2OR^2$.

The following compounds are particularly preferred:

7-[1-[(aminoacetyl)oxy]propyl]-8-methylindolizino[1,2-b]quinolin-9(11H)-one;
7-[1-[(3-amino-1-oxopropyl)oxy]propyl]-8-methylindolizino[1,2-b]quinolin-9(11H)-one;
8-methyl-7-[1-[(2-pyrrolidinylcarbonyl)oxy]propyl]indolizino[1,2-b]quinolin-9(11H)-one;
7-[1-[[2-amino-3-(1H-imidazol-4-yl)-1-oxopropyl]oxy]propyl]-8-methylindolizino[1,2-b]quinolin-9(11H)-one;
7-[1-[(2-amino-3-methyl-1-oxobutyl)oxy]propyl]-8-methylindolizino[1,2-b]quinolin-9(11H)-one;
7-[1-[(2-amino-2-methyl-1-oxopropyl)oxy]propyl]-8-methylindolizino[1,2-b]quinolin-9(11H)-one;
7-[1-[(aminoacetyl)oxy]propyl]-2-cyano-8-methylindolizino-[1,2-b]quinolin-9(11H)-one;
8-methyl-7-[1-[[(2-pyrrolidinylcarbonyl)aminoacetyl]oxy]propyl]indolizino[1,2-b]quinolin-9(11H)-one;
8-methyl-7-[1-[[(dimethylamino)acetyl]oxy]propyl]indolizino[1,2-b]quinolin-9(11H)-one;
7-[1-[[(1,4'-bipiperidin-1'-yl)acetyl]oxy]propyl]-8-methylindolizino[1,2-b]quinolin-9(11H)-one;
8-methyl-7-[1-[(4-morpholinylacetyl)oxy]propyl]indolizino[1,2-b]quinolin-9(11H)-one;
8-methyl-7-[1-[[(4-methylpiperazin-1-yl)acetyl]oxy]propyl]indolizino[1,2-b]quinolin-9(11H)-one;
7-[1-[[(1-imidazolyl)acetyl]oxy]propyl]-8-methylindolizino[1,2-b]quinolin-9(11H)-one;
8-methyl-7-[1-[(pyridinioacetyl)oxy]propyl]indolizino[1,2-b]quinolin-9(11H)-one iodide;
7-[1-[[4-[(dimethylamino)methyl]benzoyl]oxy]propyl]-8-methylindolizino[1,2-b]quinolin-9(11H)-one;
8-Methyl-7-[1-[[4-(pyridiniomethyl)benzoyl]oxy]propyl]indolizino[1,2-b]quinolin-9(11H)-one trifluoroacetate;
8-[[(4-morpholinoacetyl)oxy]methyl]-7-(1-oxopropyl)indolizino[1,2-b]quinolin-9(11H)-one;
7-[1-[[(aminomethyl)hydroxyphosphinyl]oxy]propyl]-8-methylindolizino[1,2-b]quinolin-9(11H)-one;
12-[[(aminoacetyl)oxy]methyl]-8-methyl-7-(1-oxopropyl)indolizino[1,2-b]quinolin-9(11H)-one;
8-methyl-12-[[(4-morpholinoacetyl)oxy]methyl]-7-(1-oxopropyl)indolizino[1,2-b]quinolin-9(11H)-one;
8-methyl-7-[1-[(phosphono)oxy]propyl]inodlizino[1,2-b]quinolin-9(11H)-one; and
8-[[(dimethylaminoacetyl)oxy]methyl]-7-(1-oxopropyl)indolizino[1,2-b]quinolin-9(11H)-one.

Some compounds used in the method for treating viral infections according to the present invention are known. The publications listed herein discussing the preparation of such compounds are incorporated herein by reference. The compounds of the present invention can be prepared by several means from known starting materials or by adding the appropriate substituent to the starting materials used in published synthetic methods for making camptothecin. The preferred synthetic methods for preparing the inventive compounds are outlined in the following reaction flow charts.

In general, the inventive compounds are prepared by opening the lactone ring of camptothecin or a camptothecin derivative which may have the desired $R^7$–$R^{11}$ substituent to obtain an 8-methyl-7-(1-oxopropyl)indolizino[1,2-b]quinolin-9(11H)-one. Alternatively, the lactone ring may be opened and then the $R^7$–$R^{11}$ substituents introduced. In yet another alternative method, an existing $R^7$–$R^{11}$ group is modified to obtain the desired compound. Once the lactone ring is opened, the resulting X and Y groups may be further modified as needed to make the subject compounds.

Starting materials are commercially available or can be made by published methods. Camptothecin, 10-hydroxycamptothecin and 9-hydroxycamptothecin are natural products. Camptothecin and 10-hydroxycamptothecin are available from sources in the People's Republic of China. A 9-hydroxycamptothecin compound which can be used as starting material for making some of the inventive compounds is described in Published Japanese Patent Application No. 59-51,289. The syntheses of 9- and 12-nitrocamptothecins are described by Wall, et al. (*J. Med. Chem.* 1986, 29, 2358). A total synthesis of camptothecin is described by Wall, et al., *J. Med. Chem.* 1980, 23, 554. The 1980 Wall, et al. synthesis can be used as a means to introduce one or more $R^7$–$R^{11}$ substituents into the compounds of Formula I. This involves modifying the Wall synthesis at the appropriate step in a manner which puts in place the desired substituent, then continuing with the described synthesis.

The ring-opening reaction is illustrated by Scheme 1. For the sake of convenience, all reaction schemes shown herein are illustrated with compounds which are substituted with —H at $R^7$–$R^{11}$. However, these methods also apply to compounds of the present invention having any other combination of $R^7$–$R^{11}$ substituents as defined herein above, including compounds in which one or more substituents may require protection during chemical reactions and deprotection thereafter, as is well-known to those of ordinary skill in the art.

Scheme 1

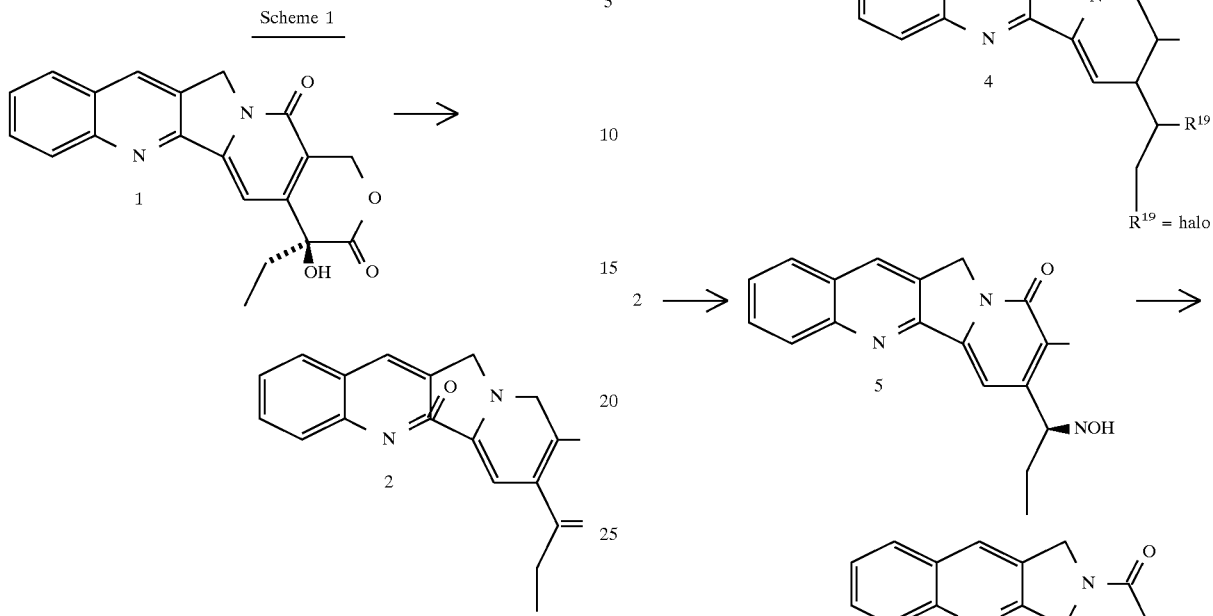

Compounds of formula 1 are converted to compounds of formula 2 by heating the compounds in a high boiling, preferably unreactive, solvent such as N,N-dimethylformamide or triglyme (triethylene glycol dimethyl ether).

As shown in Scheme 2 the keto group of compounds of formula 2 can be reduced to give the corresponding hydroxy compounds 3 from which the halo compounds 4 can be derived. The keto group also can be converted to an oxime (compounds 5) which can in turn be reduced to give the primary amino compounds 6. The keto group also can be converted to a ketal group such as a 1,3-dioxolane (compounds 7, which are useful intermediates for further transformations). The hydroxyl group of compounds 3 can also be acylated to produce esters, carbonates, and carbamates (8) or phosphorylated to produce phosphates and phosphonates (9) wherein $R^{20}$ and $R^{21}$ are groups convertible into $R^{14}$ and $R^{15}$ respectively, by either deprotection or further elaboration by well-known methods.

Scheme 2

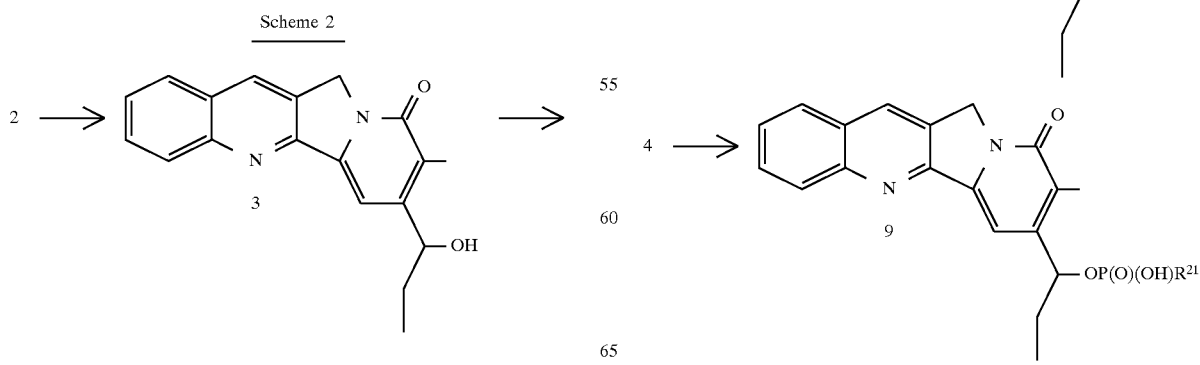

-continued
Scheme 2

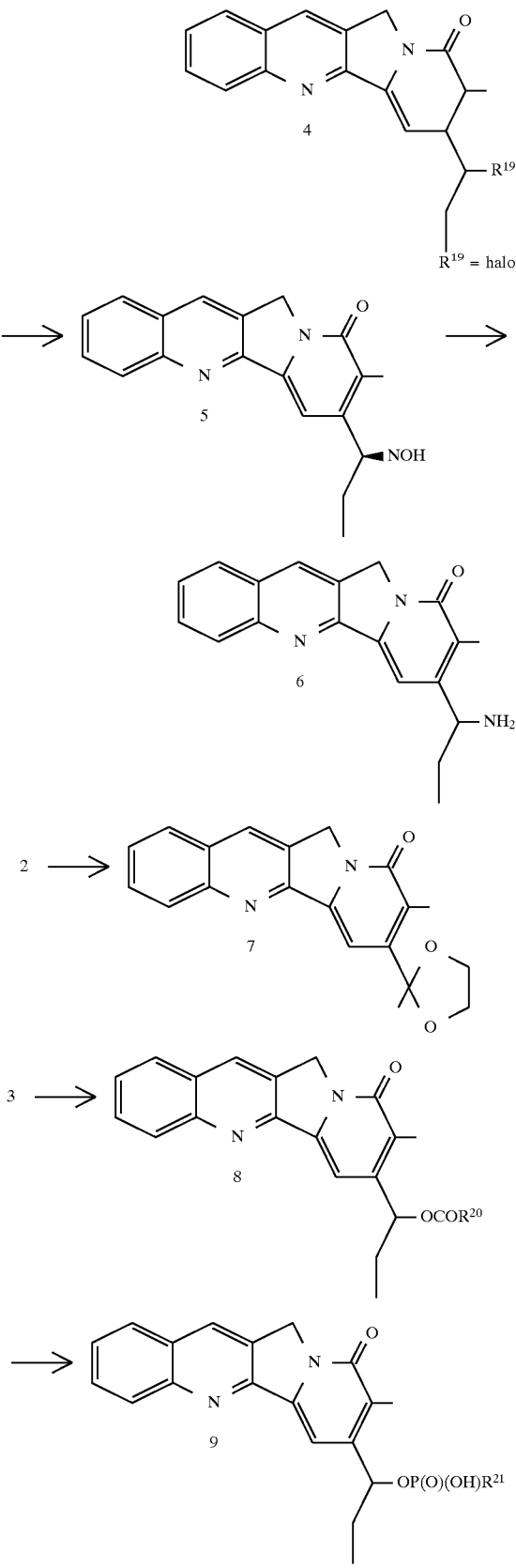

As illustrated in Scheme 3, dehydration of alcohols 3 gives alkenes 10 which can be hydroxylated to diols 11. Oxidative cleavage of the diols generates aldehydes 12 which may be covalently solvated by water or an alcoholic solvent to produce compounds of formula 13. Hydride reduction of compounds of formula 12 and 13 give the primary alcohols 14.

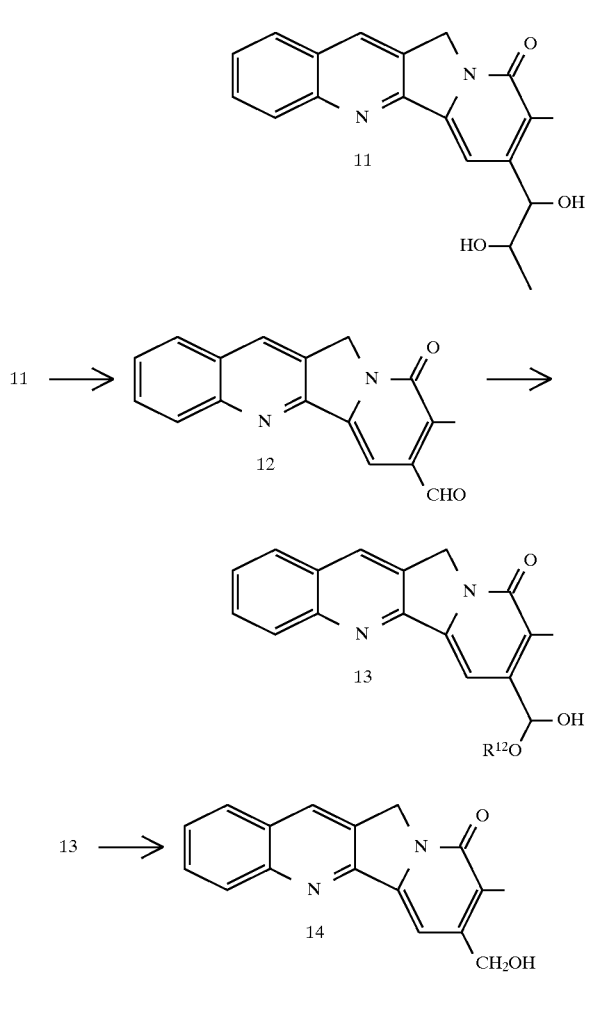

Also derived from camptothecins are the a-hydroxy acids 15 which are formed by hydrogenolytic cleavage of the lactone ring as shown in Scheme 4.

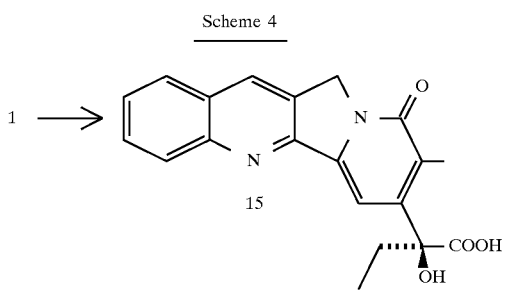

Some ring substituents may be labile to the conditions used in the preferred method of making compounds 2 as given in Scheme 1. To make compounds which are unstable under those conditions, the sequence set out in Scheme 5 can provide access to certain of those compounds or provide intermediates for making other compounds.

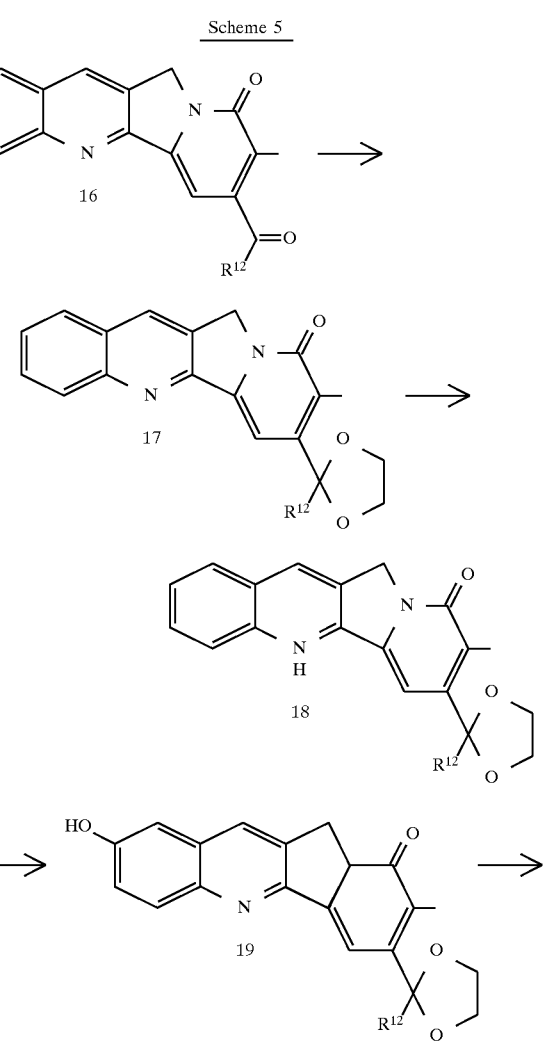

Scheme 5 -continued

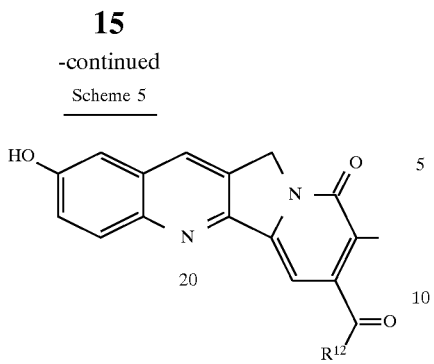

More specifically, the carbonyl group of compounds 16 is first protected as a ketal (17), and then the pyridine ring is reduced to give compounds 18, for example with sodium cyanoborohydride in an acidic solvent such as acetic acid. Finally, oxidation of compounds 18, for example by iodobenzene diacetate, gives the 2-hydroxy ketals 19 which along with the keto compounds 20 derived from the ketals by acid hydrolysis can be used to make compounds with other substituents as illustrated in Scheme 6.

Scheme 6

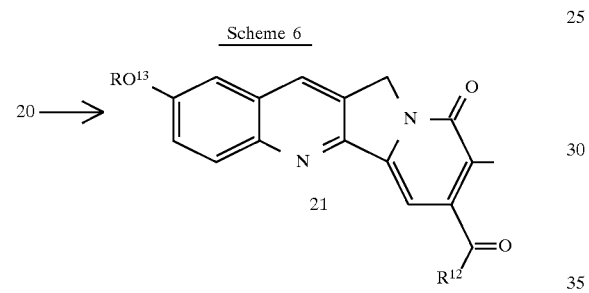

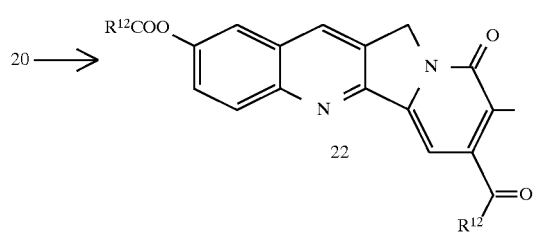

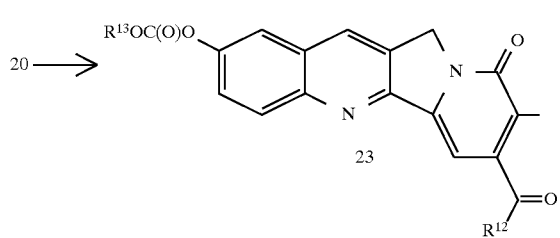

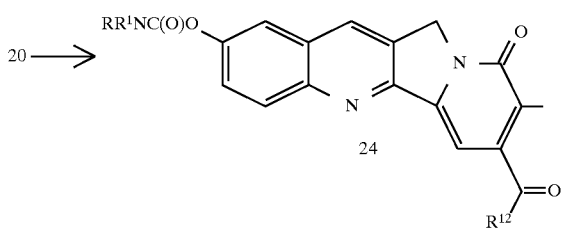

Scheme 6 -continued

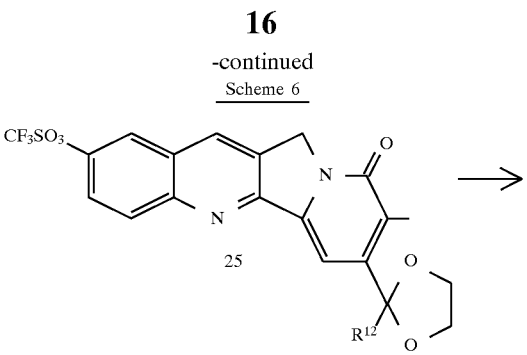

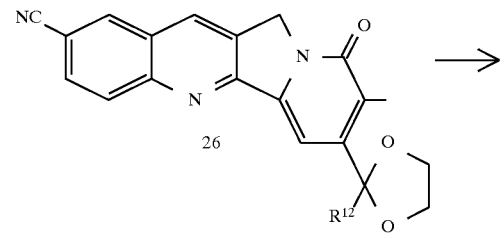

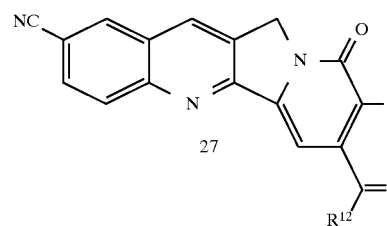

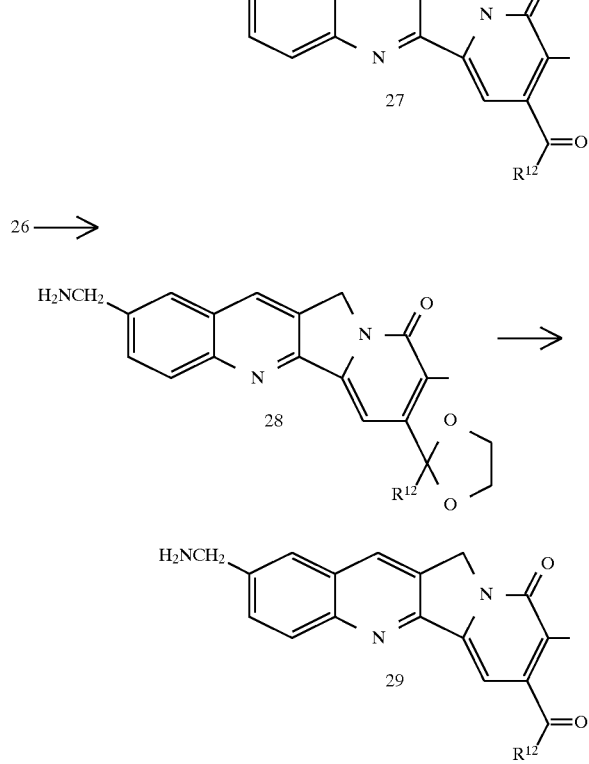

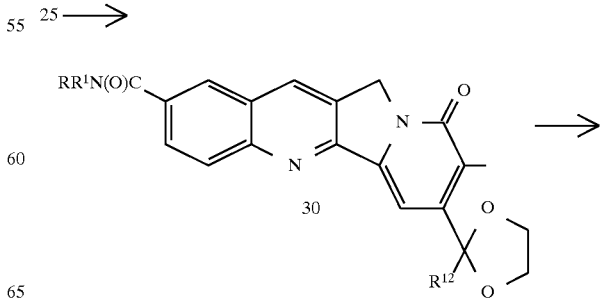

-continued
Scheme 6
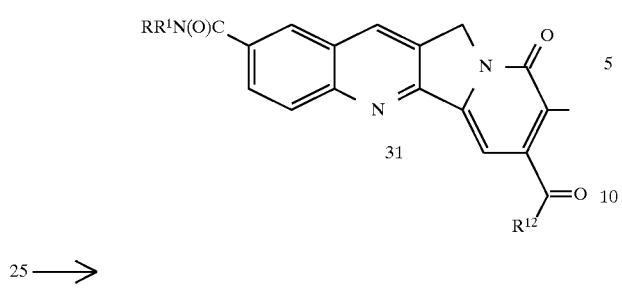
25 ⟶
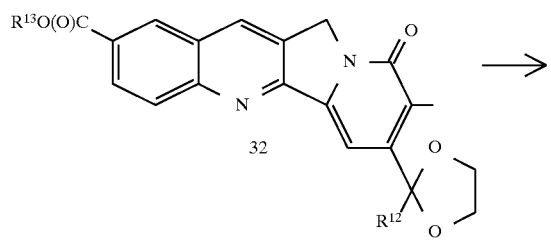
32 ⟶
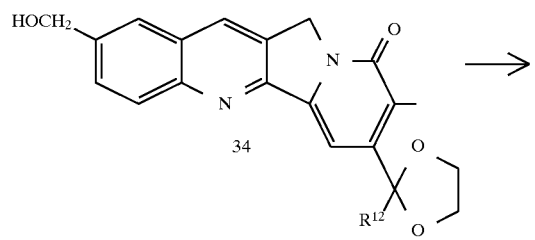
34 ⟶
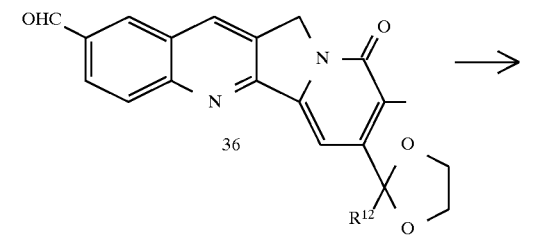
-continued
Scheme 6
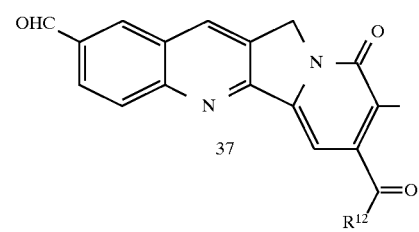
25 ⟶
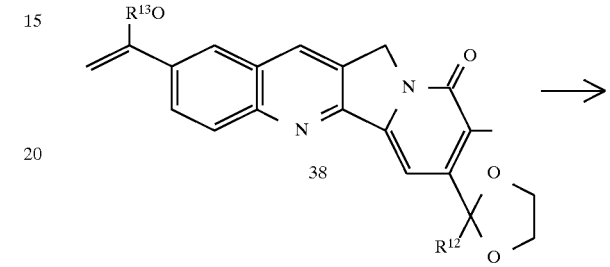
32 ⟶
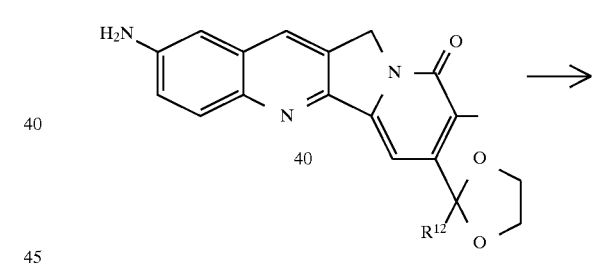
40 ⟶
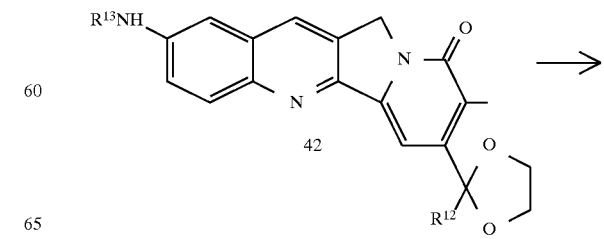

-continued
Scheme 6

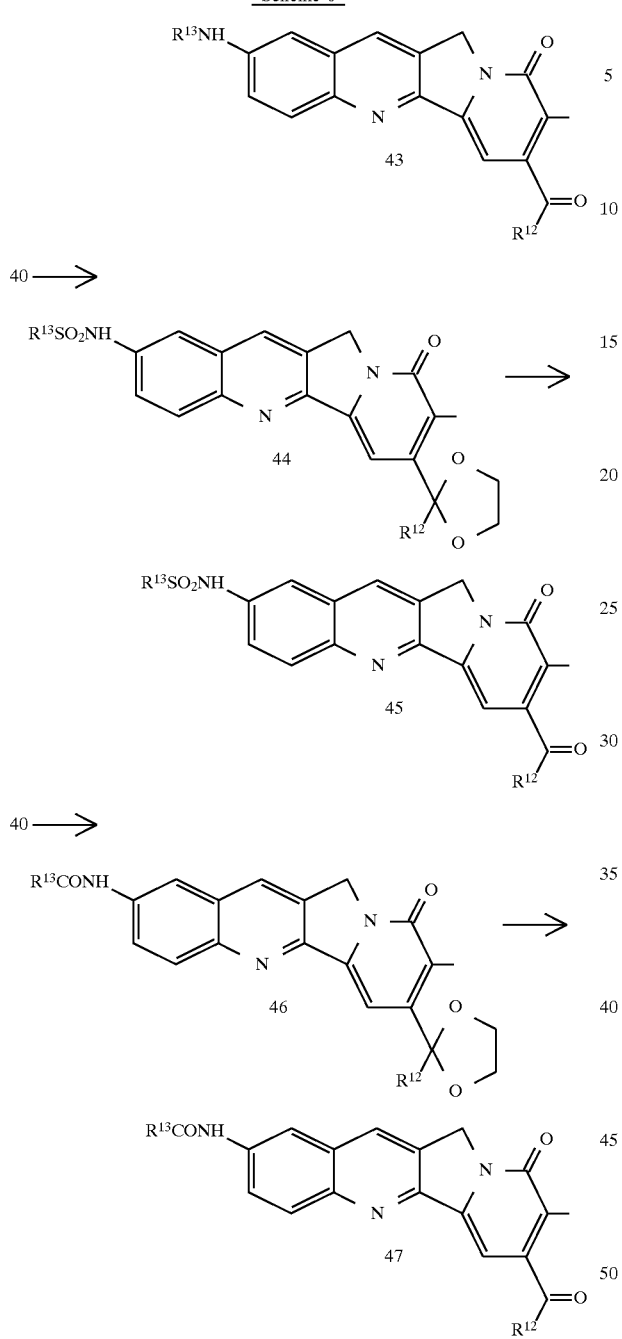

The compounds in Scheme 6 are prepared either by alkylation (compounds 21) or acylation (compounds 22, 23, and 24) of the 2-hydroxy ketones 20 or by replacement of the 2-hydroxy group in the ketals (19) via the triflates (25). Cyanation of the triflates following the method of Kosugi, M., et al, Chem. Lett. 1981, 69 gives compounds 26 which are hydrolyzed to compounds 27. Catalytic hydrogenation of the cyano group of compounds 26 gives aminomethyl ketals 28 which upon hydrolysis gives the ketones 29.

Alternatively, starting with the triflates (25), a carbonyl group can be introduced onto the ring, for example by the procedure of Cacchi, S., et al, Tetrahedron Lett. 1986, 27, 3931. If an amine or alcohol is used, the corresponding amides (30) or esters (32) are obtained which are then hydrolyzed to the respective keto compounds 31 and 33. Reduction of the esters 32 with a hydride gives the primary alcohols 34 which upon hydrolysis produce the keto alcohols 35 which can be acylated to give carboxylates, carbonates and carbamates or phosphorylated to give phosphates or phosphonates by methods similar to those used for preparing such derivatives from compounds 3. Aldehydes (compounds 36) can be made by oxidizing the alcohols 34 using a mild oxidant which gives the aldehyde in preference to the acid (for example, $MnO_2$). Deprotection gives the keto aldehydes 37.

Similarly, the triflates are converted to vinyl ethers 38 following the method of Cabri, W., et al. (J. Org. Chem. 1990, 55, 3654), and then compounds 38 are hydrolyzed to diketones 39. Selective hydrolysis of the enol ether function in compounds 38 produces the 2-keto compounds that can be reduced to secondary alcohols from which the ketal groups can be removed and the alcohol function acylated or phosphorylated as described for compounds 3.

Introduction of an amino group at the 2-position is accomplished by hydrolyzing esters 32, converting the resulting acids to acid halides (acid chlorides), treating the acid halides with sodium azide and heating those products followed by treatment with water to form the amines (40) which upon deblocking gives compounds 41. These amines can be alkylated (42), sulfonylated (44), or acylated (46) by known means and then deprotected to compounds 43, 45, and 47, respectively.

Compounds with a substituent at the 1-position that cannot be made by the method of Scheme 1 can be made by using the activating effect of the 2-hydroxy group in compounds 19; the hydroxy group may be retained in the product or removed. These preparations are illustrated in Scheme 7.

Scheme 7

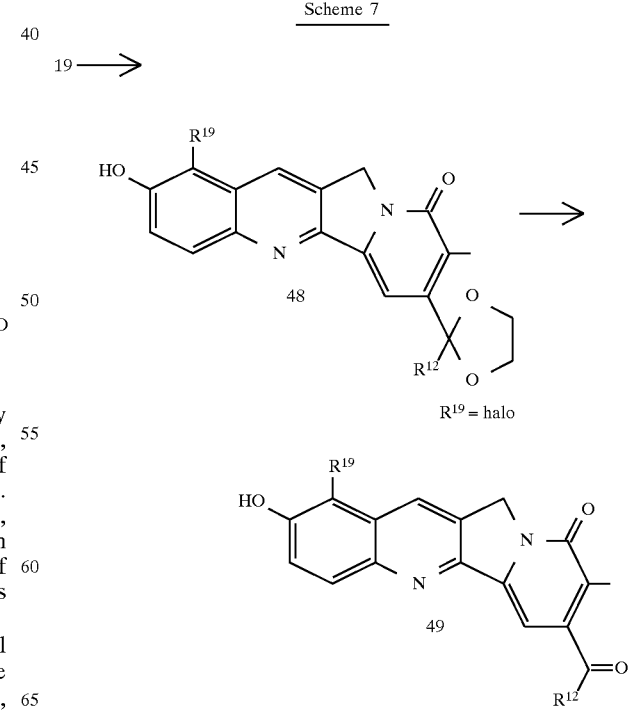

$R^{19}$ = halo

Scheme 7 -continued

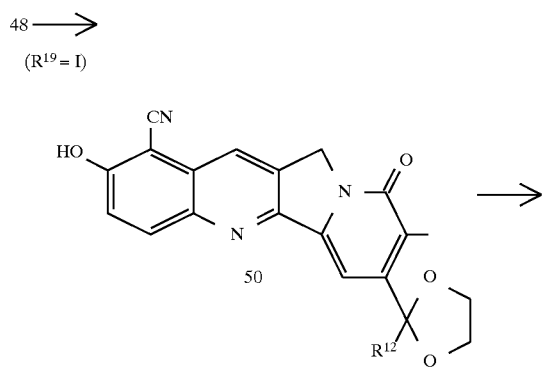

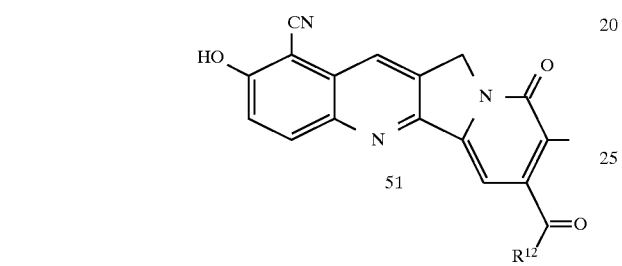

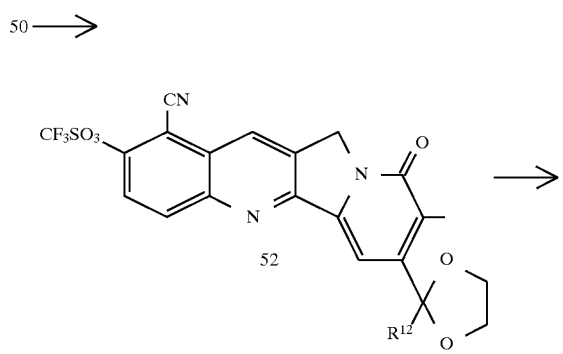

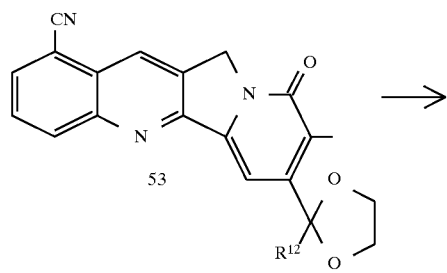

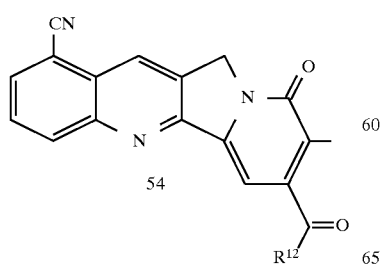

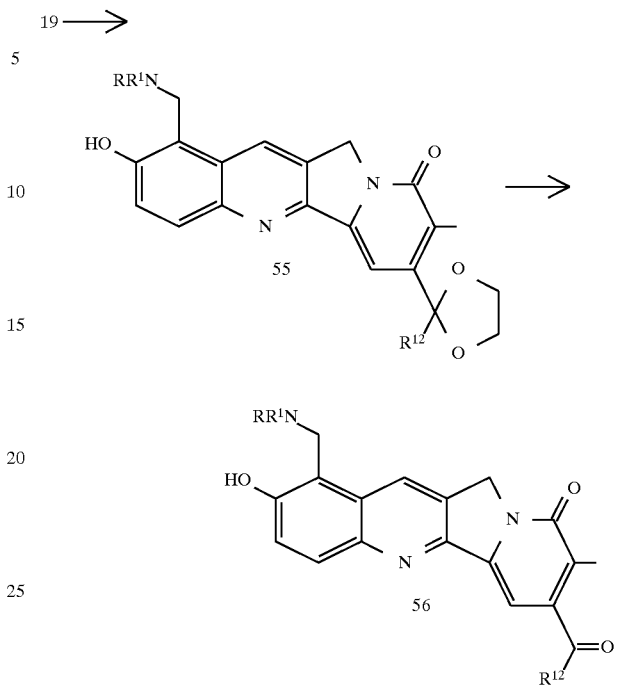

Halogenation of compounds 19 is accomplished by standard means to produce 1-halo ketals 48 which are cleaved to the corresponding ketones 49. Cyano ketals 50 are prepared using the iodides (48) in the cyanation reaction described for the synthesis of compounds 26. Cleavage of compounds 50 gives compounds 51, or alternatively, the hydroxy function can be removed from 50 by converting the compounds to the corresponding triflates 52 and then reducing them to compounds 53 by the method of Cacchi, S. et al., *Tetrahedron Lett.* 1986, 27, 5541. Hydrolysis of ketals 53 gives ketones 54.

The conversion of compounds 19 to compounds 55 is accomplished using tetramethyldiaminomethane and an acid. The dioxolane protecting group can then be hydrolyzed to obtain the keto compounds 56.

Methods for making compounds with different groups at the 7-position are illustrated in Scheme 8.

Scheme 8

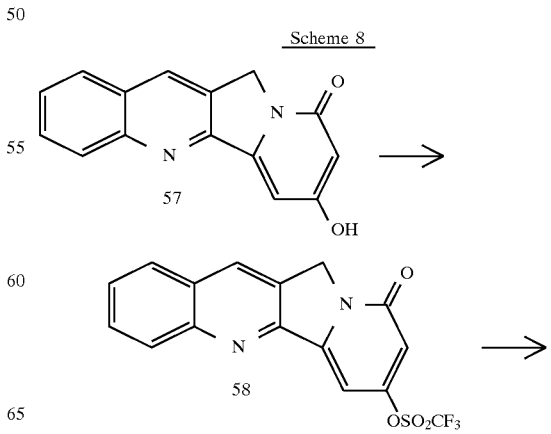

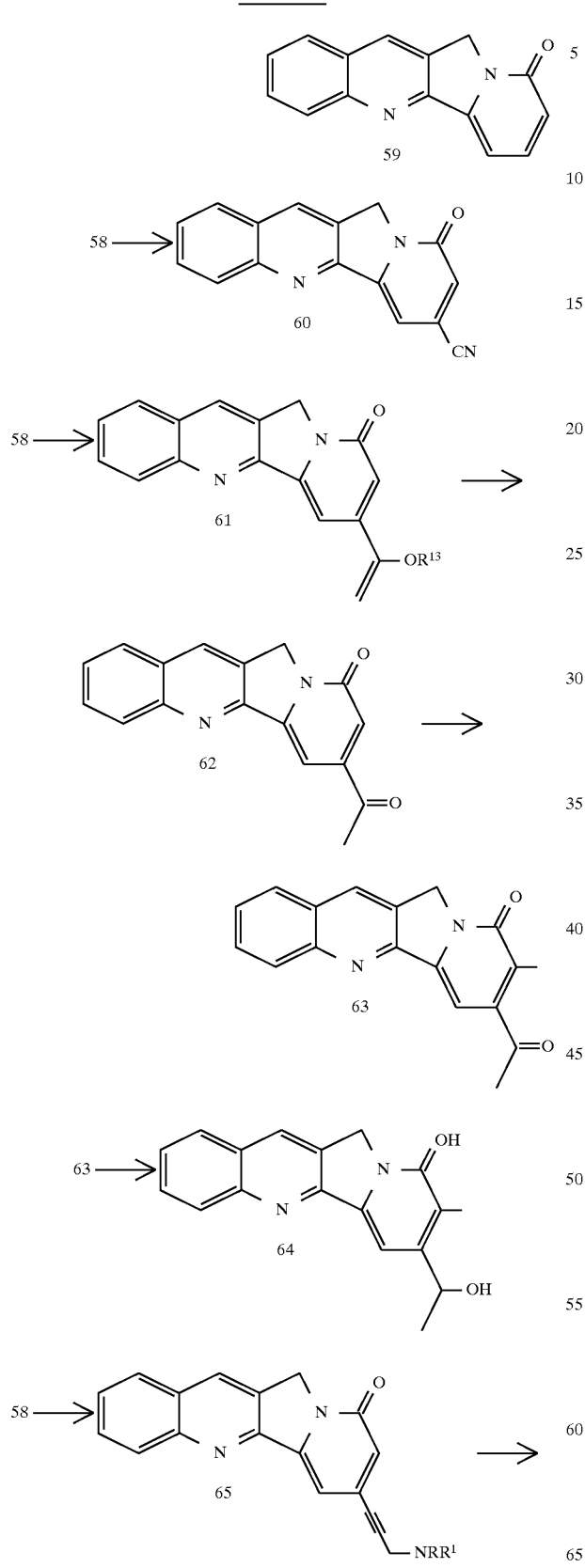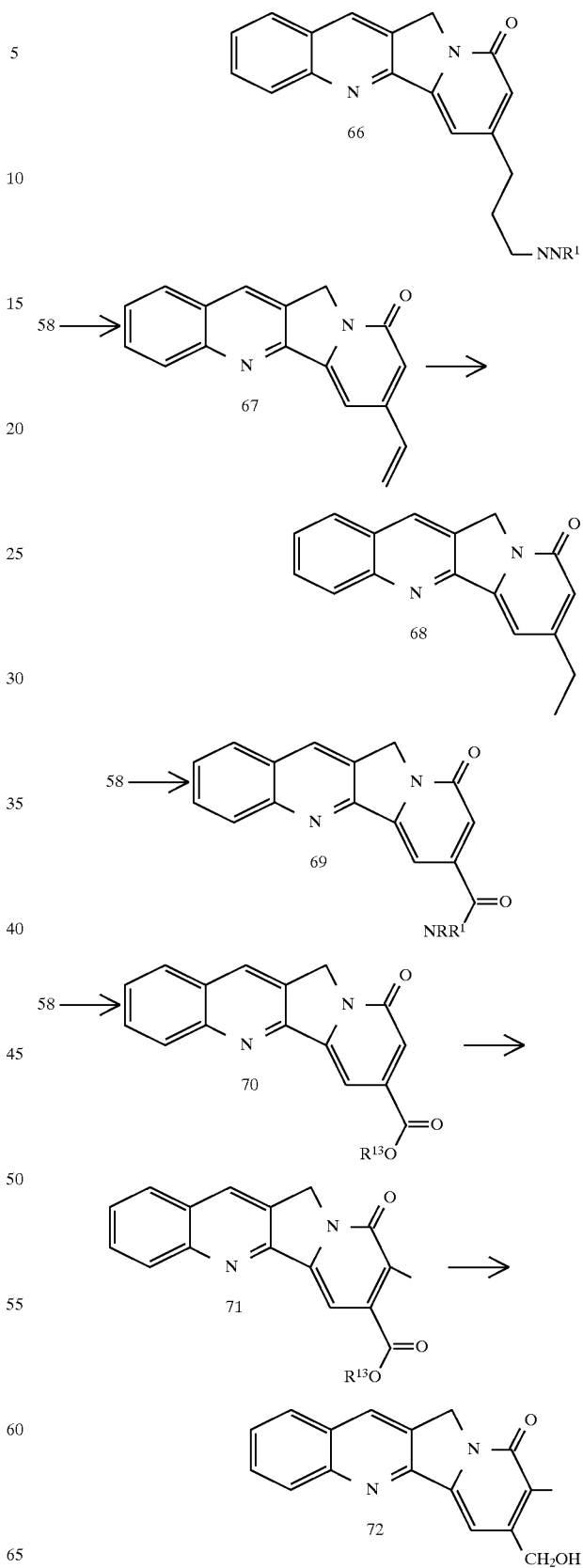

-continued
Scheme 8

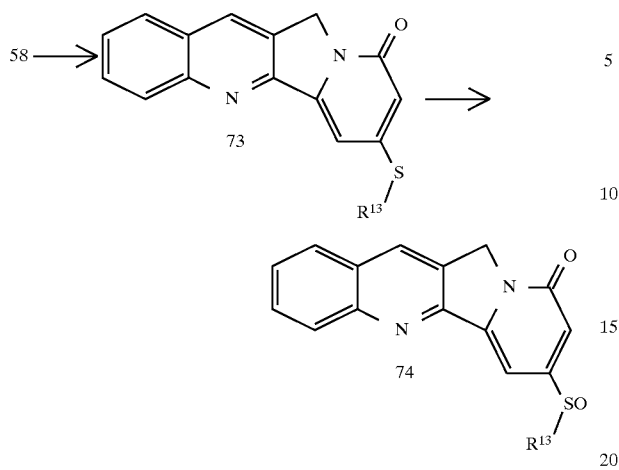

The hydroxy compounds 57 are made as described by Sugasawa, T., et al., *Chem. Pharm. Bull.* 1974, 22, 771. The triflates (58) are prepared in the usual manner. Reduction to compounds 59 is carried out by the same method used for compounds 52. Cyanation of the triflates to give compounds 60 uses the method employed to prepare compounds 26. Alkoxyvinylation of the triflates to give compounds 61 is carried out as in the preparation of compounds 38; acid hydrolysis of the vinyl ethers gives the ketones 62 which upon reaction with diazomethane by the method of Kametani, T., et al. (*Heterocycles* 1975, 3, 167) give methyl derivatives 63 which are reduced by hydrides to the alcohols 64. Coupling of the triflates with 3-dialkylaminopropyne by the method of Echavarren, A. M. and Stille, J. K. (*J. Am. Chem. Soc.* 1988, 110, 1557) gives compounds 65 which are catalytically hydrogenated to compounds 66. Vinylation of the triflates by the procedure of Chen, Q.-Y. and Yang, Z.-Y. (*Tetrahedron Lett.* 1986, 27, 1171) gives compounds 67 which are catalytically hydrogenated to ethyl compounds 68. Carbonylation of the triflates in the presence of an amine or an alcohol by the procedure used to make compounds 30 and 32 leads to amides 69 and esters 70, respectively. As described for compounds 62, compounds 70 are methylated with diazomethane to give derivatives 71 which then are reduced to alcohols 72 by hydrides. Displacement of the triflate function from compounds 58 by thiols gives sulfides 73 which are oxidized to sulfoxides 74.

Compounds with substituents in the 12-position are prepared as illustrated in Scheme 9.

Scheme 9

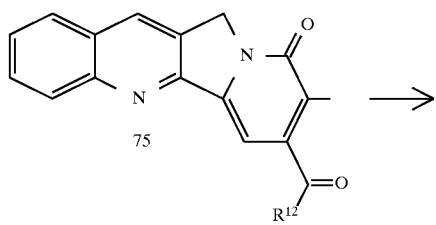

-continued
Scheme 9

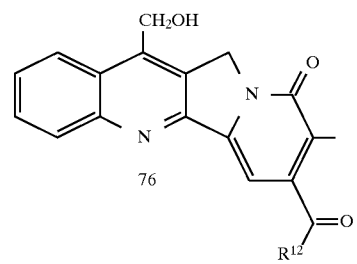

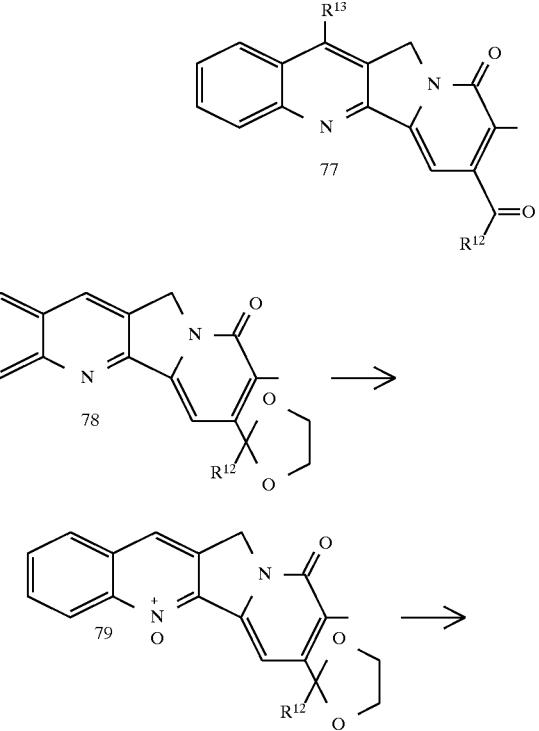

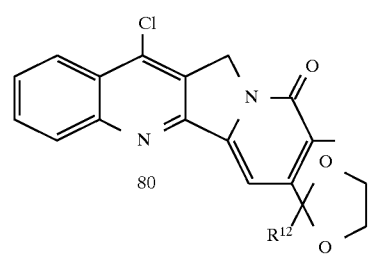

-continued
Scheme 9
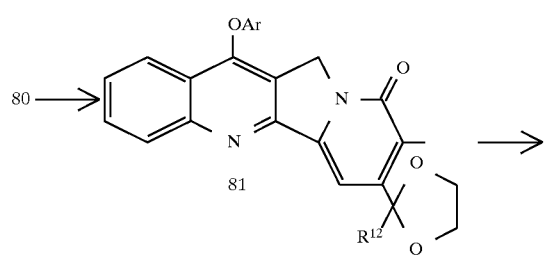
81
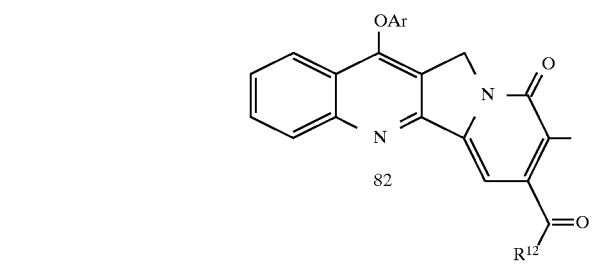
82
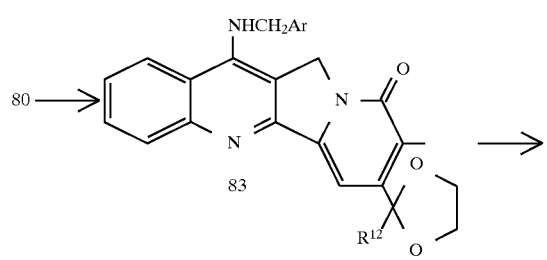
83
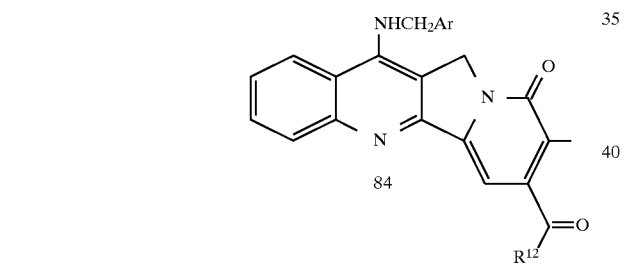
84
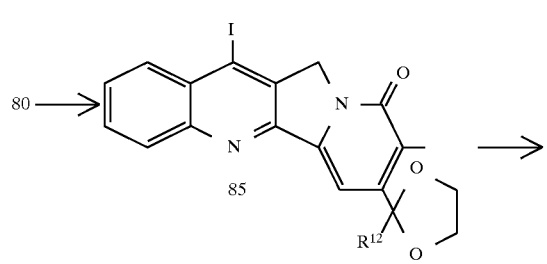
85
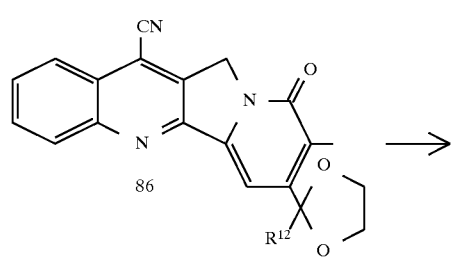
86
-continued
Scheme 9
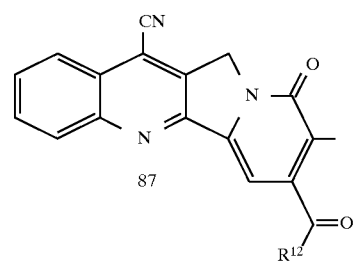
87
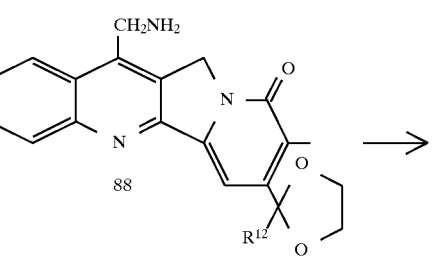
88
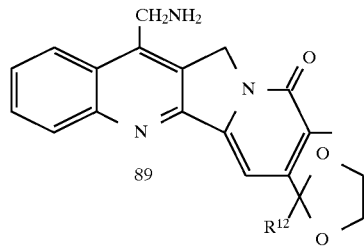
89
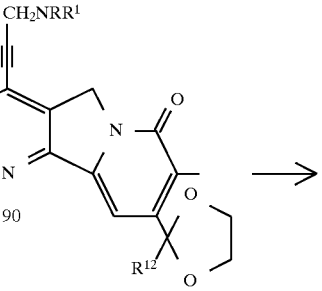
90
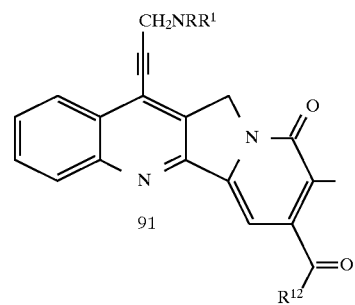
91

-continued
Scheme 9
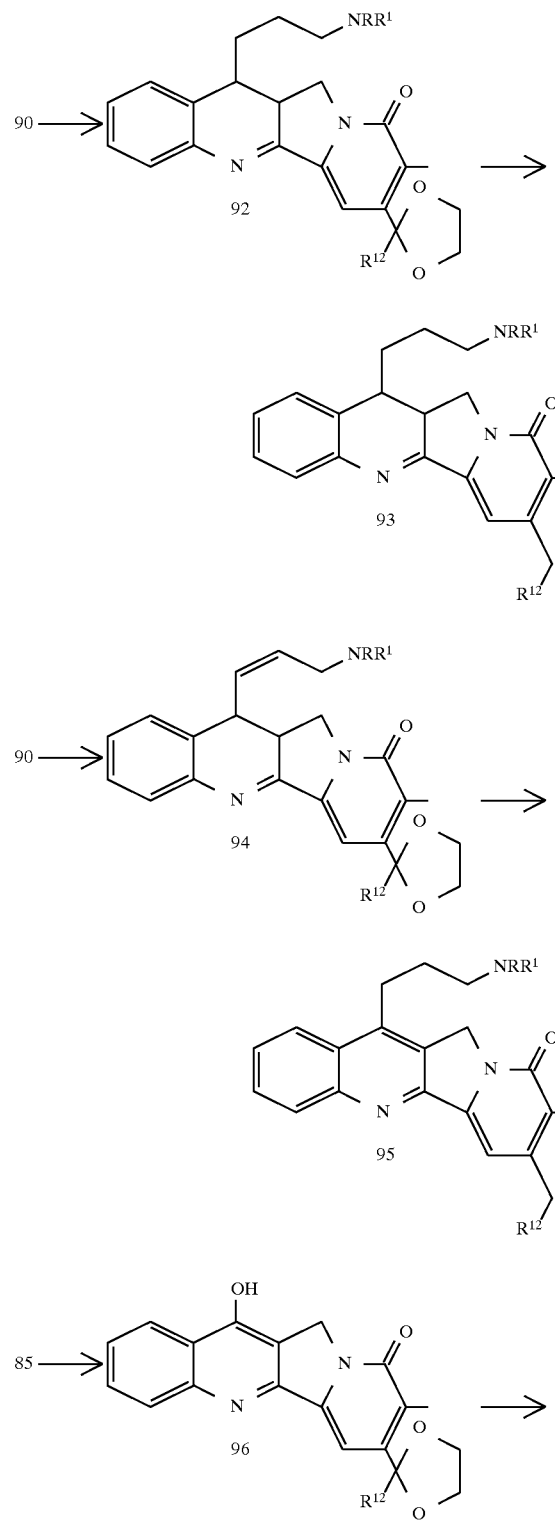
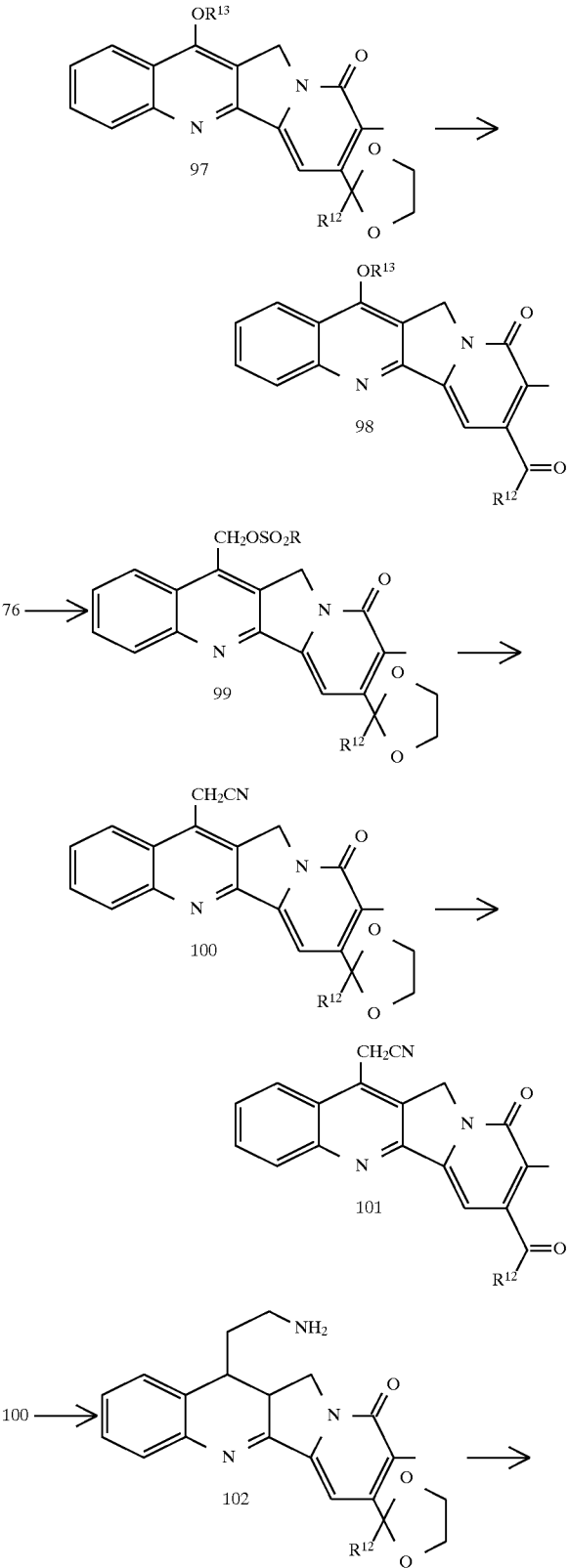

-continued
Scheme 9

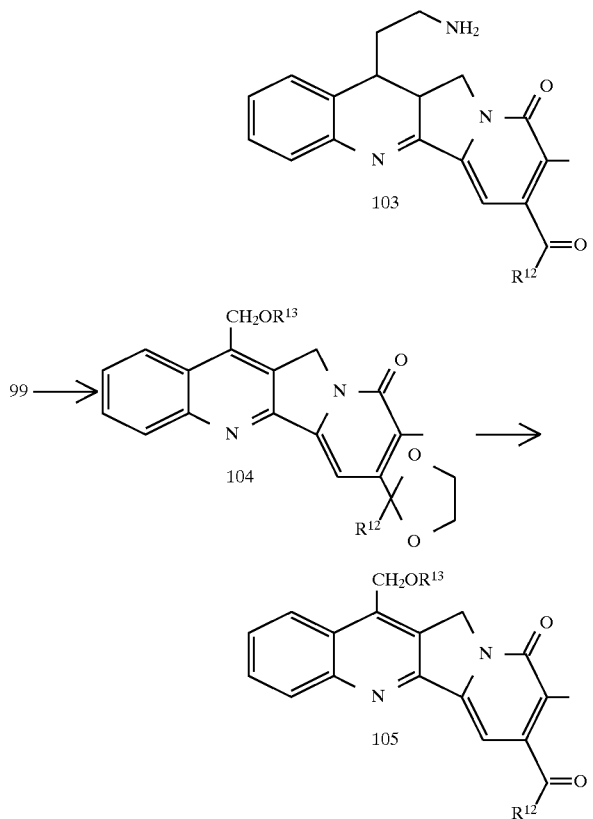

12-Hydroxymethyl compounds 76 are prepared by the method of Miyaska, T. et al. (*Heterocycles* 1981, 16, 1713) using ferrous sulfate, hydrogen peroxide and methanol with sulfuric acid. These alcohols are acylated or phosphorylated as described for compounds 3 to produce carboxylates, carbonates and carbamates, or phosphates and phosphonates. Similarly, 12-alkyl compounds 77 are prepared by the method of Miyasaka, T. et al. (U.S. Pat. No. 4,399,282).

Oxidation of compounds 78, for example, with hydrogen peroxide in acetic acid, gives the N-oxides 79 which upon heating with tosyl chloride in N,N-dimethylformamide gives the 12-chloro compounds 80 that can be converted to many other compounds. Heating of the chloro compounds with arylols, such as phenol, gives the 12-aryloxy compounds 81 which upon deprotection give the ketones 82; if, however, an aminomethylarene is included in the reaction, the products are compounds 83 which upon hydrolysis give keto compounds 84. The chloro substituent of compounds 80 can be replaced with an iodo group (85) by heating with potassium iodide in acetic acid containing some acetic anhydride. The iodo derivatives are easily used in various coupling reactions similar to those carried out with triflates 25 and 58. Cyanation gives compounds 86 which are deblocked to ketones 87 or are reduced to aminomethyl compounds 88 which give ketones 89 upon hydrolysis. Likewise, propynylamines 90 can be produced and then deprotected to compounds 91 or catalytically hydrogenated to compounds 92 and 94 which are hydrolyzed to keto compounds 93 and 95, respectively. Heating compounds 85 with sodium acetate in acetic acid gives the 12-hydroxy compounds 96 which can be alkylated using either base and alkyl halides or diazoalkanes to give 12-alkoxy compounds 97 which upon deprotection afford ketones 98. The 12-hydroxymethyl compounds 76 can be protected and then activated for displacement reactions by conversion to a sulfonate (99), for example, a mesylate. Cyanide displacement on compounds 99 gives the ketals 100 which upon hydrolysis give 12-cyanomethyl ketones 101. The cyano ketals can also be reduced to aminoethyl compounds 102 that give ketones 103 after hydrolysis. Treatment of sulfonates 99 with alcohols in the presence of bases gives ethers 104 which can be converted to keto ethers 105.

The reactions illustrated in Scheme 9 for the 12-hydroxymethyl compounds 76 could likewise be applied to hydroxymethyl compounds 34 to produce derivatives corresponding to compounds 99 through 105.

As shown in Scheme 10, compounds 107, the open ring form of compounds 106, which are described in co-pending U.S. Ser. No. 07/839,823, are acylated or phosphorylated as described for compounds 3 to give compounds 108 and 109, respectively.

Scheme 10

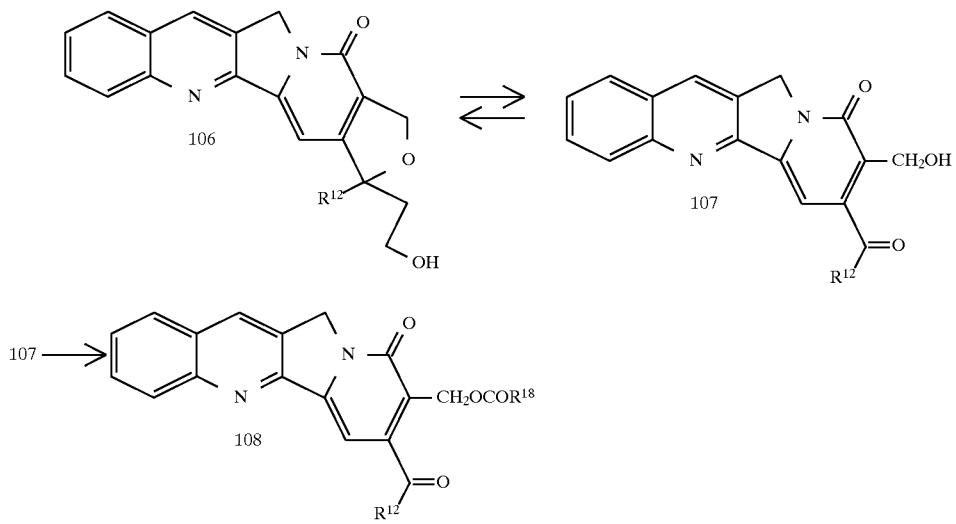

-continued
Scheme 10

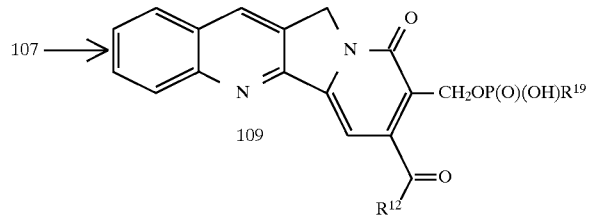

The compounds of the present invention exhibit antiviral activity and are generally useful in treating DNA replicating animal virus infections, particularly those caused by viruses in the herpes family. More specifically, these compounds are useful in treating infections caused by the following human pathogens:

Herpes Simplex virus types 1 and 2;
Cytomegalovirus;
Varicella Zoster virus;
Epstein Barr virus; and
Papilloma virus (multiple types).

Infections caused by the following animal pathogens may also be treated with the present compounds:

Equine Herpes virus;
Porcine Herpes virus;
Marek's disease virus;
Feline Rhinotracheitis virus; and
Bovine Herpes virus.

Assays

The assay used to test the compounds of the present invention for antiviral activity was taken from the literature and was modified in well-known ways to adapt it to currently available technology. A generalized description of the assay follows.

Assay Procedure

Well plates were seeded with the appropriate cells at a concentration of $1\times10^5$ cells per well suspended in 0.5 mL of Earle's Minimum Essential Medium (EMEM) containing 10% fetal bovine serum (FBS) and antibiotic and antimycotic solution. After cells were 80–90% confluent (24 hours), old medium was removed and washed with Hank's buffered saline solution (HBSS). Cells were then infected for 1 hour at 37° C. with 100–200 plaque forming units per well of a herpes simplex virus suspended in 250 mL HBSS. Following adsorption, the following were added:

A) 250 mL/well 2×EMEM containing Human IgG (ca 0.1 mg/mL; Sigma No. G-6763);
B) 250 mL/well EMEM containing 10% FBS and antibiotic/antimycotic solution;
C) 250 mL/well HBSS containing appropriately diluted compound.

After 24–48 hours (optimum time determined by examination of the plaques under microscope), old medium was aspirated off. Each well was stained with a selected stain solution (0.5% crystal violet in MeOH:H$_2$O 7:3) and then rinsed with water and air dried and plaques counted. Compound effectiveness was evaluated in terms of percent plaque reduction as compared to untreated, infected controls.

This procedure can be used to test compound efficacy against many viruses besides herpes simplex by simply modifying the cell type used in the first step to match the virus being tested and following the procedure outlined above. Other cell types which could be used in this assay include mouse mammary tumor cells, human lung fibroblasts, sheep chorioplexus cells, and green monkey kidney cells.

Other assays which are useful for determining the antiviral activity of the present compounds include the following types: cell count, clonogenic, cytopathic effect, dish-colony formation, microtiter-growth inhibition, thymidine incorporation and yield reduction. Each of these well-known assays is in the literature and selected assays are available commercially.

Pharmaceutical Compositions and Method of Treatment

The present invention provides a broad variety of compositions prepared from compounds of the present invention. Such compositions have utility for human and veterinary antiviral use, and for treating viral infections in plants, e.g., agricultural or ornamental seeds and plants. Such compositions comprise a carrier which is acceptable for the intended end use together with at least one inventive compound. For example, in veterinary use, the carrier may be a liquid, or spray, or may be formulated in a solid, non-degradeable or degradeable form for insertion in the rumen. For agricultural use, the compound can be mixed with a fertilizer, other microbiocides such as fungicides, or insecticides and the like. The present compounds may also be formulated in powders or sprays for application to plant surfaces.

The pharmaceutical compositions of this invention comprise one or more compounds of the present invention in admixture with an inert pharmaceutically acceptable carrier or diluent. Compositions may contain an effective amount of the inventive compound in one unit, such as in a single pill, capsule, or pre-measured intravenous dose or pre-filled syringe for injection, or, as is frequently the case, the composition may be prepared in individual dose forms where one unit, such as a pill, contains a sub-optimal dose with the user being instructed to take two or more unit doses per treatment. When the composition is presented as a cream, it contains a discrete amount of drug and the user applies an effective amount of the cream one or more times until the disease is in remission or has been effectively treated. Concentrates for later dilution by the end user may also be prepared, for instance for IV formulations and multi-dose injectable formulations.

Carriers or diluents contemplated for use in these compositions are generally known in the pharmaceutical formulary arts. Reference to useful materials can be found in well known compilations such as *Remington's Pharmaceutical Sciences*, Mack Publishing Co., Easton, Pa., 18042, U.S.A.

The nature of the composition and the pharmaceutically acceptable carrier or diluent will, of course, depend upon the intended route of administration, for example, by intravenous and intramuscular injection, parenterally, topically, orally, or by inhalation.

For parenteral administration the pharmaceutical composition may be in the form of a sterile injectable liquid such as an ampule or an aqueous or nonaqueous liquid suspension.

For topical administration the pharmaceutical composition may be in the form of a cream, ointment, liniment, lotion, paste, spray or drops suitable for administration to the skin, eye, ear, nose or genitalia.

For oral administration the pharmaceutical composition may be in the form of a tablet, capsule, powder, pellet, atroche, lozenge, syrup, liquid, or emulsion.

The pharmaceutically acceptable carrier employed may be either a solid or liquid. Exemplary of solid carriers are lactose, kaolin, terra alba, sucrose, talc, gelatin, agar, pectin, acacia, magnesium stearate, mannitol, stearic acid and the like.

Examples of appropriate pharmaceutically acceptable liquid carriers or diluents include: for aqueous systems, water; for non-aqueous systems, ethanol, glycerin, propylene glycol, corn oil, cottonseed oil, peanut oil, sesame oil, liquid paraffins and mixtures thereof with water. For aerosol systems, pharmaceutically acceptable carriers include dichlorodifluoromethane, chlorotrifluoroethylene and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions. Similarly, the carrier or diluent may include time delay materials well known to the art, such as glyceryl monostearate or glyceryl distearate alone or with a wax, ethylcellulose, hydroxypropylmethylcellulose, methylmethacrylate and the like.

To obtain a stable water soluble dose form, a pharmaceutically acceptable salt of a compound of the present invention is dissolved in an aqueous solution of an organic or inorganic acid or base. If a soluble salt form is not available, the inventive compound may be dissolved in a suitable co-solvent or combinations thereof. Examples of such suitable cosolvents include, but are not limited to, alcohol, propylene glycol, polyethylene glycol 300, polysorbate 80, glycerin and the like in concentrations ranging from 0–60% of the total volume.

It will be appreciated that the actual preferred dosages of the compounds of the present invention used in the pharmaceutical and other compositions of this invention will vary according to the particular complex being used, the particular composition formulated, the mode of administration and the particular site, host and disease being treated. These compounds are active in the concentration ranges of two commercial antiviral drugs, Cytovene (ganciclovir) and Zovirax (acyclovir). For example, the latter is manufactured in 200 mg capsules with instructions for treating herpes simplex viruses by taking one capsule every 4 hours, but not to exceed 5 capsules per day.

In the following Examples, temperature is in degrees Centigrade (°C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

EXAMPLE 1

(±)-1-Methoxy-7-(1-hydroxypropyl)-8-methylindolizino[1,2-b]quinolin-9(11H)-one

A solution of 1-methoxy-8-methyl-7-(1-oxopropyl) indolizino[1,2-b]quinolin-9(11H)-one (5.0 mg, 15 μmol) in a mixture of MeOH (0.2 mL), $CH_2Cl_2$ (0.6 mL) and THF (0.2 mL) was treated with a single portion of sodium borohydride (4.0 mg, 110 μmol). After stirring at room temperature for 1.5 h, the reaction mixture was concentrated under reduced pressure. The residue was treated with 10% aqueous $NH_4Cl$ (350 μL) and allowed to stand at 4° C. overnight. The solid which formed was collected by filtration, washed sparingly with $H_2O$ and dried to afford the title compound. $^1H$ NMR ($CDCl_3/MeOH-d_4$) d 8.77 (s, 1H), 7.69 (m, 2H), 7.59 (s, 1H), 6.92 (dd, J=6.8, 1.7 Hz, 1H), 5.23 (br s, 2H), 4.89 (m, 1H), 4.05 (s, 3H), 2.24 (s, 3H), 1.79 (m, 2H), 1.03 (t, J=7.4 Hz, 3H).

EXAMPLE 2

(±)-2-Cyano-7-(1-hydroxypropyl)-8-methylindolizino[1,2-b]quinolin-9(11H)-one

The title compound was prepared according to the procedure in Example 1 except using 2-cyano-8-methyl-7-(1-oxopropyl)indolizino[1,2-b]quinolin-9(11H)-one. $^1H$ NMR ($CDCl_3/MeOH-d_4$) d 8.29 (s, 1H), 8.32 (d, J=1.7 Hz, 1H), 8.20 (d, J=8.9 Hz, 1H), 7.92 (dd, J=8.8, 1.8 Hz, 1H), 7.67 (s, 1H), 5.30 (br s, 2H), 4.91 (m, 1H), 2.26 (s, 3H), 1.79 (m, 2H), 1.03 (t, J=7.4 Hz, 3H). Anal. Calcd for $C_{20}H_{17}N_3O_2 \cdot H_2O$: C, 68.75; H, 5.48; N, 12.03, Found: C, 68.97; H, 5.26; N, 11.72.

EXAMPLE 3

(±)-7-[1-[(Aminoacetyl)oxy]propyl]-8-methylindolizino[1,2-b]quinolin-9(11H)-one Hydrotrifluoroacetate 3A. (±)-8-Methyl-7-[1-[[[[(1,1-dimethylethoxy)carbonyl] amino]-acetyl]oxy]propyl]indolizino[1,2-b]quinolin-9(11H)-one To a suspension of N-[(1,1-dimethylethoxy)carbonyl] glycine (1.15 g, 6.6 mmol) in $CH_2Cl_2$ (50 mL) under an argon atmosphere was added 1,3-dicyclohexylcarbodiimide (1.35 g, 6.5 mmol). After stirring at room temperature for 0.5 h, (±)-7-(1-hydroxypropyl)-8-methylindolizino[1,2-b] quinolin-9(11H)-one (1.0 g, 3.3 mmol) was added followed by a few mg of 4-dimethylaminopyridine. The resulting mixture was allowed to stir at room temperature overnight and then was filtered. The filtrate was washed successively with 2.5% aqueous $NaHCO_3$ (100 mL), 0.1N HCl (100 mL) and $H_2O$ (100 mL), dried over sodium sulfate and concentrated in vacuo. The solid residue was purified by column chromatography on silica gel eluting with a solvent gradient of 0–2% $MeOH/CH_2Cl_2$ to provide the title compound. $^1H$ NMR ($CDCl_3$) d 8.34 (s, 1H), 8.21 (d, J=8.8 Hz, 1H), 7.91, (d, J=8.3 Hz, 1H), 7.81, (m, 1H), 7.63, (m 1H), 7.32 (s, 1H), 5.96 (apparent br t, J=7.0 Hz, 1H), 5.25 (s, 2H), 5.03 (br s, 1H), 4.15–3.94 (m, 2H), 2.36 (s, 3H), 2.04–184 (m, 2H), 1.44 (s, 9H), 0.99 (t, J=7.4 Hz, 3H). Anal. Calcd for $C_{26}H_{29}N_3O_5 \cdot 1/8\ H_2O$: C, 67.04; H, 6.33; N, 9.02. Found: C, 66.95; H, 6.54; N, 8.83.

3B. (±)-7-[1-[(Aminoacetyl)oxy]propyl]-8-methylindolizino[1.2-b]quinolin-9(11H)-one Hydrotrifluoroacetate To a stirring suspension of (±)-8-methyl-7-[1-[[[[(1,1-dimethylethoxy)carbonyl]amino]acetyl]oxy]propyl] indolizino[1,2-b]quinolin-9(11H)-one (1.15 g, 2.5 mmol) in 1,3-dimethoxybenzene (12 mL) under an argon atmosphere was added trifluoroacetic acid (13 mL). After stirring for 1.5 h at room temperature, the mixture was concentrated under reduced pressure. The residue was dissolved in $H_2O$, extracted with $Et_2O$, filtered and lyophilized to afford the title compound as a pale yellow solid. $^1$H NMR (DMSO-$d_6$) d 8.68 (s, 1H), 8.24 (m, 1H), 8.13 (m, 1H), 7.86 (apparent br t, 1H), 7.70 (apparent br t, 1H), 7.19 (s, 1H), 5.91 (apparent br t, 1H), 5.26 (s, 2H), 4.02 (br s, 2H), 2.25 (s, 3H), 2.06–1.81 (m, 2H), 0.96 (t, J=7.2Hz, 3H). Anal. Calcd for $C_{21}H_{21}N_3O_3 \cdot CF_3CO_2H \cdot 9/4 H_2O$: C, 53.33; H, 5.16; N, 8.11. Found: C, 53.09; H, 4.91; N, 7.74.

EXAMPLE 4

(±)-7-[1-[(3-Amino-1-oxopropyl)oxy]propyl]-8-methylindolizino[1,2-b]quinolin-9(11H)-one Hydroacetate 4A. (±)-8-Methyl-7-[1-[[3-[[(1,1-dimethylethoxy)carbonyl] amino]-1-oxopropyl]oxy]propyl]indolizino[1,2-b]quinolin-9(11H)-one A mixture containing (±)-7-(1-hydroxypropyl)-8-methylindolizino[1,2-b]quinolin-9(11H)-one (61.2 mg, 0.20 mmol), 4-dimethylaminopyridine (7.4 mg, 0.06 mmol), 4-nitrophenyl 3-[[(1,1-dimethylethoxy)carbonyl]amino] propionate (248 mg, 0.80 mmol) and dry triethylamine (222 mL, 1.60 mmol) in 1,2-dichloroethane (5 mL) under an argon atmosphere was heated at reflux for 5 d. Thin layer chromatographic analysis at this time indicated that the reaction was incomplete, so the mixture was transferred to a pressure bottle and heated at 90°–95° C. for 1 d. Afterwards, additional 4-nitrophenyl 3-[[(1,1-dimethylethoxy)carbonyl]amino]propionate (248 mg, 0.80 mmol) and dry triethylamine (222 mL, 1.60 mmol) were added, and heating was continued for 13 d. The mixture was then purified by flash chromatography eluting with a solvent gradient of 0–3% MeOH/$CH_2Cl_2$. The material that was isolated was recrystallized from $Et_2O$ and dried in vacuo to afford the title compound, mp 155°–8° C. $^1$H NMR ($CDCl_3$) d 8.35 (s, 1H), 8.22 (d, J=8.6 Hz, 1H), 7.91 (d, J=7.2 Hz, 1H), 7.81 (m, 1H), 7.63 (m, 1H), 7.32 (s, 1H), 5.90 (dd, J=7.7, 6.1 Hz, 1H), 5.26 (s, 2H), 5.02 (br s, 1H), 3.44 (m, 2H), 2.66 (q, J=5.8 Hz, 2H), 2.02–1.80 (m, 2H), 1.38 (s, 9H), 0.98 (t, J=7.4 Hz, 3H). Anal. Calcd for $C_{27}H_{31}N_3O_5 \cdot 1/5 H_2O$: C, 67.40; H, 6.58; N, 8.73. Found: C, 67.78; H, 6.48; N, 8.35.

4B. (±)-7-[1-[(3-Amino-1-oxopropyl)oxy]propyl]-8-methylindolizino[1,2-b]quinolin-9(11H)-one Hydroacetate The title compound was prepared according to the procedure in Example 3B except using (±)-8-methyl-7-[1-[[3-[[(1,1-dimethylethoxy)carbonyl]amino]-1-oxopropyl]oxy] propyl]indolizino[1,2-b]quinolin-9(11H)-one with the product being purified by reversed phase chromatography on Partisil 40 ODS-3 eluting with a gradient of 0–100% MeOH in $H_2O$ containing 1% acetic acid. $^1$H NMR ($CDCl_3$/MeOH-$d_4$) d 8.42 (s, 1H), 8.20 (d, J=8.4 Hz, 1H), 7.96 (d, J=8.3 Hz, 1H), 7.84 (m, 1H), 7.67 (m, 1H), 7.43 (s, 1H), 5.92 (dd, J=7.7, 6.0 Hz, 1H), 5.28 (s, 2H), 3.02 (br s, 2H), 2.69 (apparent br t, J=5.9 Hz, 2H), 2.36 (s, 3H), 2.02 (s, 3H), 2.02–1.82 (m, 2H), 1.01 (t, J=7.4 Hz, 3H). CIMS ($NH_3$, m/e, rel. int.) 378 (100) [(M+H)$^+$]. Anal. Calcd for $C_{22}H_{23}N_3O_3 \cdot C_2H_4O_2 \cdot 13/4 H_2O$: C, 58.11; H, 681; N, 8.47. Found: C, 58.22; H, 6.13; N, 8.10.

EXAMPLE 5

8-Methyl-7-[1-[(-2-pyrrolidinylcarbonyl)oxy]propyl] indolizino[1,2-b]quinolin-9(11H)-one Hydrotrifluoroacetate and Separation of Isomers 5A. (R,S)-8-Methyl-7-[1-[[(S)1-[(1,1-dimethylethoxy) carbonyl]-2-pyrrolidinylcarbonyl]oxy]propyl]indolizino[1, 2-b]quinolin-9(11H)-one The title compound was prepared according to the procedure in Example 3A except using N-[(1,1-dimethylethoxy)carbonyl]-L-proline, N,N'-diisopropylcarbodiimide and (±)-7-(1-hydroxypropyl)-8-methylindolizino[1,2-b]quinolin-9(11H)-one.

5B. (R,S)-8-Methyl-7-[1[((S)-2-pyrrolidinylcarbonyl)oxy] propyl]indolizino[1,2-b]quinolin-9(11H)-one Hydrotrifluoroacetate To a mixture containing (R,S)-8-methyl-7-[1-[[(S)1-[(1, 1-dimethylethoxy)carbonyl]-2-pyrrolidinylcarbonyl]oxy] propyl]indolizino[1,2-b]quinolin-9(11H)-one (1.66 g, 3.3 mmol) in $CH_2Cl_2$ (50 mL) was added trifluoroacetic acid (10 mL). The resulting mixture was allowed to stir at room temperature for 1.5 h and then was concentrated under reduced pressure. The residue was dissolved in $H_2O$ (150 mL) and lyophilized to afford the title compound as a mixture of diastereomers. $^1$H NMR ($D_2O$) d 7.68 and 7.64 (2 s, 1H), 7.45 and 7.36 (two d, 1H), 7.33–6.95 (m, 3H), 6.94 and 6.91 (two s, 1H), 5.93 (m, 1H), 4.9–4.6 (m obscured by HOD peak), 4.2–3.9 (m, 2H), 3.52 and 3.43 (overlapping m and t, 2H), 2.73–2.55 (m, 1H), 2.45–1.95 (m, 5H), 2.12 and 2.06 (two s, 3H), 1.08 (m, 3H). Anal. Calcd for $C_{24}H_{25}N_3O_3 \cdot 11/4 CF_3CO_2H$: C, 49.41; H, 3.90; N, 5.86. Found: C, 49.84; H, 4.16; N, 6.00.

5C. (S)-8-Methyl-7-[1-[((S)-2-pyrrolidinylcarbonyl)oxy] propyl]indolizino[1,2-b]quinolin-9(11H)-one Hydrotrifluoroacetate The diastereomeric mixture of (R,S)-8-methyl-7-[1-[((S) -2-pyrrolidinylcarbonyl)oxy]propyl]indolizino[1,2-b] quinolin-9(11H)-one was purified by preparative chromatography (JY column packed with 2 kg 15–20 mm Vydac $C_{18}$ RP silica), eluting with 0.1/25/75 TFA/$CH_3CN$/$H_2O$. The title compound was the first to elute and was obtained after solvent removal under reduced pressure and lyophilization. $^1$H NMR ($D_2O$) d 7.99 (s, 1H), 7.75 (d, J=8.5 Hz, 1H), 7.57 (m, 1H), 7.51 (d, J=8.2 Hz, 1H), 7.33 (m, 1H), 7.20 (s, 1H), 6.09 (dd, J=7.9, 5.6 Hz, 1H), 4.9–4.7 (m obscured by HOD peak), 4.52 (d, J=18.9Hz, 1H), 4.40 (d, J=18.8 Hz, 1H), 3.53 (t, J=7.3 Hz, 2H), 2.75 (m, 1H), 2.45–2.08 (m, 5H), 2.30 (s, 3H), 1.19 (t, J=7.4 Hz, 3H). Anal. Calcd for $C_{24}H_{25}N_3O_3 \cdot 2 CF_3CO_2H \cdot 1/4 H_2O$: C, 52.88; H, 4.36; N, 6.61. Found: C, 52.76; H, 4.50; N, 6.64.

5D. (R-)-8-Methyl-7-[1-[((S)-2-pyrrolidinylcarbonyl)oxy] propyl]indolizino[1,2-b]quinolin-9(11)-one Hydrotrifluoroacetate The remaining fractions from the separation process in Example 5C were combined and concentrated under reduced pressure. The title compound was obtained after an additional preparative chromatographic separation using the conditions in Example 5C. $^1$H NMR ($D_2O$) d 8.00 (s, 1H), 7.68 (d, J=8.5 Hz, 1H), 7.56–7.49 (m, 2H), 7.32 (m, 1H), 7.19 (s, 1H), 6.09 (dd, J=8.0, 5.2 Hz, 1H), 4.93–4.67 9 m obscured by HOD peak), 4.49 (d, J=18.9 Hz, 1H), 4.40 (d, J=19.0 Hz, 1H), 3.66–3.57 (m, 2H), 2.78 (m, 1H), 2.47 (m, 1H), 2.29 (m, 2H), 2.24 (s, 3H, 2.15 (m, 2H), 1.17 (t, 3H). Anal. Calcd for $C_{24}H_{25}N_3O_3 \cdot 7 CF_3CO_2H \cdot 4 H_2O$: C, 35.83; H, 3.17; N, 3.30. Found: C, 35.86; H, 3.24; N, 3.64.

5E. (R,S)-8-Methyl-7-[1[[(R)-1-[(1,1-dimethylethoxy) carbonyl[-2-pyrrolidinylcarbonyl]oxy]propyl]indolizino[1, 2-b]quinolin-9(11H)-one To a mixture of N-[(1,1-dimethylethoxy)carbonyl]-D-proline (6.74 g, 31.3 mmol) in $CH_2Cl_2$ (47 mL) under an argon atmosphere was added dicyclohexylcarbodiimide (3.22 g, 15.6 mmol). After stirring at room temperature for 2 h, the mixture was filtered and concentrated under reduced pressure to afford N-[(1,1-dimethylethoxy)carbonyl]-D-proline anhydride. This was added to a suspension of (±)-7-(1-hydroxypropyl)-8-methylindolizino[1,2-b] quinolin-9(11H)-one (1.50 g, 4.9 mmol) and 4-dimethylaminopyridine (609 mg, 5.0 mmol) in $CH_2Cl_2$ (450 mL), and the mixture was allowed to stir at room temperature under an argon atmosphere overnight. The reaction mixture was washed with $H_2O$ (2×), dried over potassium carbonate and concentrated under reduced pressure. The residue was purified by flash chromatography eluting with a solvent gradient of 0–2% $MeOH/CHCl_3$ to afford the title compound.

5F. (R,S)-8-Methyl-7-[1-[((R)-2-pyrrolidinylcarbonyl)oxy]propyl]indolizino[1,2-b]quinolin-9(11H)-one Hydrotrifluoroacetate The title compound was prepared according to the procedure in Example 5B except using (R,S)-8-methyl-7-[1-[[(R)-1-[(1,1-dimethylethoxy)carbonyl]-2-pyrrolidinylcarbonyl]oxy]propyl]indolizino[1,2-b]quinolin-9(11H)-one. $^1$NMR was essentially identical to that of the compound of Example 5B. Anal. Calcd for $C_{24}H_{25}N_3O_3.2 CF_3CO_2H$: C, 53.25; H, 4.31; N, 6.65. Found: C, 53.07; H, 4.68; N, 7.02.

5G. (R)-8-Methyl-7-[1[((R)-2-pyrrolidinylcarbonyl)oxy]propyl]indolizino[1,2-b]quinolin-9(11H)-one Hydrotrifluoroacetate The title compound was obtained by separation of the diastereomers of (R,S)-8-methyl-7-[1-[((R)-2-pyrrolidinylcarbonyl)oxy]propyl]indolizino[1,2-b]quinolin-9(11H)-one according to the procedure in Example 5C. Anal. Calcd for $C_{24}H_{25}N_3O_3.3 CF_3CO_2H.H_2O$: C, 47.19; H, 3.96; N, 5.50. Found: C, 47.24; H, 4.30; N, 5.83.

5H. (S)-8-Methyl-7-[1[((R)-2-pyrrolidinylcarbonyl)oxy]propyl]indolizino[1.2-b]quinolin-9(11H)-one Hydrotrifluoroacetate The title compound was obtained by separation of the diastereomers of (R,S)-8-methyl-7-[1-[((R)-2-pyrrolidinylcarbonyl)oxy]propyl]indolizino[1,2-b]quinolin-9(11H)-one according to the procedure in Example 5C. Anal. Calcd for $C_{24}H_{25}N_3O_3.8/3 CF_3CO_2H.H_2O$: C, 48.56; H, 4.12; N, 5.79. Found: C, 48.61; H, 4.53; N, 6.10.

EXAMPLE 6

(R,S)-7-[1-[[(S)-2-Amino-3-(1H-imidazol-4-yl)-1-oxopropyl]oxy]propyl]-8-methylindolizinol[1,2-b]quinolin-9(11H)-one Hydrotrifluoroacetate 6A. (R,S)-8-Methyl-7-[1-[[(S)-2-[[(1,1-dimethylethoxy)carbonyl]amino]-3-(1H-imidazol-4-yl)-1-oxopropyl]oxy]prop]indolizino[1,2-b]quinolin-9(11H)-one The title compound was prepared according to the procedure in Example 3A except using N,1-bis[(1,1-dimethylethoxy)carbonyl]-L-histidine,N,N'-diisopropylcarbodiimide and (±)-7-(1-hydroxypropyl)-8-methylindolizino[1,2-b]quinolin-9(11H)-one.

6B. (R,S)-7-[1-[[(S)-2-Amino-3-(1H-imidazol-4-yl)-1-oxopropyl]oxy]propyl]-8-methylindolizino[1,2-b]quinolin-9(11H)-one Hydrotrifluoroacetate The title compound was prepared according to the procedure in Example 5B except using (R,S)-8-methyl-7-[1-[[(S)-2-[[(1,1-dimethylethoxy)carbonyl]amino]-3-(1H-imidazol-4-yl)-1-oxopropyl]oxy]propyl]indolizino[1,2-b]quinolin-9(11H)-one and was purified by preparative MPLC eluting first with 0.1 % $TFA/H_2O$ followed by a solvent gradient of 20–50% MeOH in $H_2O$ containing 0.1% TFA. $^1$H NMR ($D_2O$) d 8.64 and 8.35 (two s, 1H), 8.22 (d, 1H), 7.90 (d, 1H), 7.70 (m, 2H), 7.45 (m, 2H), 7.20 (s, 1H), 6.04 (m, 1H), 4.9–4.6 (m obscured by HOD peak), 3.68–3.47 (m, 2H), 2.23 and 2.19 (two s, 3H), 2.15–1.96 (m, 2H), 1.04 and 0.96 (two t, 3H). Anal. Calcd for $C_{25}H_{25}N_5O_3.2.8 CF_3CO_2H$: C, 48.18; H, 3.67; N, 9.18. Found: C, 48.29; H, 3.93; N, 9.15.

EXAMPLE 7

(±)-7-[1-[(2-Amino-3-methyl-1-oxobutyl)oxy]propyl]-8-methylindolizinol[1.2-b]quinolin-9(11H)-one Hydrotrifluoroacetate 7A. (±)-8-Methyl-7-[1-[[2-[[(1.1-dimethylethoxy)carbonyl]amino]-3-methyl-1-oxobutyl]oxy]propyl]indolizino[1,2-b]quinolin-9(11H)-one The title compound was prepared according to the procedure in Example 3A except using N-[(1,1-dimethylethoxy)carbonyl]-L-valine and (±)-7-(1-hydroxypropyl)-8-methylindolizino[1,2-b]quinolin-9(11H)-one. $^1$H NMR ($CDCl_3$) d 8.34 (s, 1H), 8.22 (m, 1H), 7.91 (d, J=8.2 Hz, 1H), 7.80 (m, 1H), 7.62 (m, 1H), 7.34 (two s, 1H), 5.94 (m, 1H), 5.26 (s, 2H), 5.04 (two br d, J=9.3 Hz, 1H), 4.36 (two d, J=4.5 Hz, 1H), 2.36 (s, 3H), 2.4–2.2 (m, 1H), 2.1–1.8 (m, 2H), 1.44 and 1.38 (two s, 9H), 1.00 (overlapping t and d, 9H).

7B. (±)-7-[1-[(2-Amino-3-methyl-1-oxobutyl)oxy]propyl]-8-methylindolizino[1,2-b]quinolin-9(11H)-one Hydrotrifluoroacetate The title compound was prepared according to the procedure in Example 3B except using (±)-8-methyl-7-[1-[[2-[[(1,1-dimethylethoxy)carbonyl]amino]-3-methyl-1-oxobutyl]oxy]propyl]indolizino[1,2-b]quinolin-9(11H)-one. $^1$H NMR ($CDCl_3$, MeOH-$d_4$) d 8.39 and 8.35 (two s, 1H), 8.20–8.13 (m, 1H), 7.94–7.81 (m, 2H), 7.66 (apparent br t, 1H), 7.41 (two s, 1H), 6.05 (m, 1H), 5.25 (s, 2H), 3.98 (two d, J=4.4 Hz, 1H), 2.55–2.36 (m, 1H), 2.33 (s, 3H), 2.14–1.90 (m, 2H), 1.15–1.01 (m, 9H). Anal. Calcd for $C_{24}H_{27}N_3O_3.CF_3CO_2H.7/4 H_2O$: C, 56.67; H, 5.76; N, 7.63. Found: C, 56.65; H, 5.62; N, 7.29.

EXAMPLE 8

(±)-7-[1-[(2-Amino-2-methyl-1-oxopropyl)oxy]propyl]-8-methylindolizino[1,2-b]quinolin-9(11H)-one Hydrotrifluoroacetate 8A. (±)-8-Methyl-7-[1-[[2-[[(1,1-dimethylethoxy)carbonyl]amino]-2-methyl-1-oxopropyl]oxy]propyl]indolizino[1,2-b]quinolin-9(11H)-one To a mixture containing 2-methyl-2-[N-[(1,1-dimethylethoxy)carbonyl]amino]propionic acid (406 mg, 2.0 mmol) and dicyclohexylcarbodiimide (432 mg, 2.0 mmol) in $CH_2Cl_2$ (3 mL) under an argon atmosphere were added (±)-7-(1-hydroxypropyl)-8-methylindolizino[1,2-b]quinolin-9(11H)-one (153 mg, 0.5 mmol) and 4-dimethylaminopyridine (25 mg). The resulting mixture was allowed to stir at room temperature for 4 d and then was poured into $CH_2Cl_2$, washed successively with 5% aqueous $NaHCO_3$, 0.5N HCl and $H_2O$, and dried over sodium sulfate. Removal of the solvent in vacuo and purification of the residue by column chromatography (silica gel) eluting with a solvent gradient of 1.5–5% $MeOH/CH_2Cl_2$ afforded the title compound as an off-white solid. $^1$H NMR ($CDCl_3$) d 8.33 (s, 1H), 8.20 (d, J=8.9 Hz, 1H), 7.90 (d, J=8.3 Hz, 1H), 7.80 (m, 1H), 7.62 (m, 1H), 7.33 (s, 1H), 5.92 (dd, J=7.5, 6.3 Hz, 1H), 5.25 (s, 2H), 5.10 (br s, 1H), 2.38 (s, 3H), 2.08–1.82 (m, 2H), 1.56 (s, 3H), 1.55 (s, 3H), 1.41 (s, 9H), 0.99 (t, J=7.4 Hz, 3H).

8B. (±)-7-[1-[(2-Amino-2-methyl-1-oxopropyl)oxy]propyl]-8-methylindolizino[1,2-b]quinolin-9(11H)-one Hydrotrifluoroacetate The title compound was prepared according to the procedure in Example 3B except using (±)-8-methyl-7-[1-[[2-[[(1,1-dimethylethoxy)carbonyl]amino]-2-methyl-1-oxopropyl]oxy]propyl]indolizino[1,2-b]quinolin-9(11H)-one. $^1$H NMR (DMSO-$d_6$) d 8.67 (s, 1H), 8.11 (m, 2H), 7.84

(m, 1H), 7.70 (m, 1H), 7.21 (s, 1H), 5.85 (dd, J=7.9, 5.8 Hz, 1H), 5.25 (s, 2H), 2.24 (s, 3H), 2.1–1.83 (m, 2H), 1.52 (s, 3H), 1.49 (s, 3H), 0.97 (t, J=7.3 Hz, 3H). Anal. Calcd for $C_{23}H_{25}N_3O_3 \cdot CF_3CO_2H \cdot 2\ H_2O$: C, 55.45; H, 5.58; N, 7.76. Found: C, 55.85; H, 5.19; N, 7.83.

EXAMPLE 9

(±)-7-[1-[(Aminoacetyl)oxy]propyl]-2-cyano-8-methylindolizino[1,2-b]quinolin-9(11H)-one Hydrotrifluoroacetate 9A. (±)-2-Cyano-8-methyl-7-[1-[[[[(1,1-dimethylethoxy) carbonyl]amino]acetyl]oxy]propyl]indolizino[1,2-b] quinolin-9(11H)-one The title compound was prepared according to the procedure in Example 3A except using (±)-2-cyano-7-(1-hydroxypropyl)-8-methylindolizino[1,2-b]quinolin-9(11H)-one.

9B. (±)-7-[1-[(Aminoacetyl)oxy]propyl]-2-cyano-8-methylindolizino[1,2-b]quinolin-9(11H)-one The title compound was prepared according to the procedure in Example 3B except using (±)-2-cyano-8-methyl-7-[1-[[[[(1,1-dimethylethoxy)carbonyl]amino]acetyl]oxy] propyl]indolizino[1,2-b]quinolin-9(11H)-one. $^1$H NMR (DMSO-$d_6$) d 8.81 (d, J=1.5 Hz, 1H), 8.77 (s, 1H), 8.27 (d, J=8.9 Hz, 1H), 8.13 (dd, J=8.9, 1.8 Hz, 1H), 7.24 (s, 1H), 5.91 (apparent br t, J=6.7 Hz, 1H), 5.29 (s, 2H), 3.98 (br s, 2H), 2.26 (s, 3H), 2.05–1.81 (m, 2H), 0.96 (t, J=7.4 Hz, 3H). Anal. Calcd for $C_{22}H_{20}N_4O_3 \cdot 3/2\ CF_3CO_2H \cdot H_2O$: C, 52.00; H, 4.10; N, 9.70. Found: C, 52.04; H, 4.32; N, 9.73.

EXAMPLE 10

(±)-7-[1-[(Aminoacetyl)oxy]propyl]-12-cyano-8-methylindolizino[1,2-b]quinolin-9(11H)-one Hydrotrifluoroacetate 10A. (±)-12-Cyano-8-methyl-7-[1-[[[[(1,1-dimethylethoxy) carbonyl]amino]acetyl]oxy]propyl]indolizino[1,2-b] quinolin-9(11H)-one The title compound was prepared according to the procedure in Example 3A except using (±)-12-cyano-7-(1-hydroxypropyl)-8-methylindolizino[1,2-b]quinolin-9(11H)-one. $^1$H NMR (CDCl$_3$) d 8.31 (d J=8.5 Hz, 1H), 8.27 (d, J=8.3 Hz, 1H), 7.95 (m, 1H), 7.84 (m, 1H), 7.32 (s, 1H), 5.95 (apparent br t, J=7.0 Hz, 1H), 5.43 (s, 2H), 5.0 (br s, 1H), 4.03 (m, 2H), 2.38 (s, 3H), 0.99 (t, J=7.4 Hz, 3H).

10B. (±)-7-[1-[(Aminoacetyl)oxy]propyl]-12-cyano-8-methylindolizino[1.2-b]quinolin-9(11H)-one Hydrotrifluoroacetate The title compound was prepared according to the procedure in Example 3B except using (±)-12-cyano-8-methyl-7-[1-[[[[(1,1-dimethylethoxy)carbonyl]amino]acetyl]oxy] propyl]indolizino[1,2-b]quinolin-9(11H)-one. $^1$H NMR (CDCl$_3$/MeOH-$d_4$) d 8.28 (d, J=8.5 Hz, 1H), 8.22 (d, J=8.4 Hz, 1H), 7.95 (m, 1H), 7.82 (m, 1H), 7.36 (s, 1H), 6.00 (apparent t, J=6.6 Hz, 1H), 5.41 (s, 2H), 3.92 (br s, 2H), 2.33 (s, 3H), 2.08–1.82 (m, 2H), 1.00 (t, J=7.2 Hz, 3H). Anal. Calcd for $C_{22}H_{20}N_4O_3 \cdot 3/2\ CF_3CO_2H \cdot 5/2\ H_2O$: C, 49.67; H, 4.42; N, 9.27. Found: C, 49.41; H, 4.23; N, 9.29.

EXAMPLE 11

(R,S)-8-Methyl-7-[1-[[(S)-(2-pyrrolidinylcarbonyl) aminoacetyl]oxy]-propyl]indolizino[1,2-b]quinolin-9 (11H)-one Hydrotrifluoroacetate 11A. (R,S)-8-Methyl-7-[1-[[[[(S)1-[(1,1-dimethylethoxy) carbonyl]-2-pyrrolidinylcarbonyl]amino]acetyl]oxy]propyl] indolizino[1,2-b]-quinolin-9(11H)-one The title compound was prepared according to the procedure in Example 5E except using (±)-7-[1-[(aminoacetyl) oxy]propyl]-8-methylindolizino[1,2-b]quinolin-9(11H)-one.

11B. (R,S)-8-Methyl-7-[1-[[(S)-(2-pyrrolidinylcarbonyl) aminoacetyl]oxy]propyl]indolizino[1,2-b]quinolin-9(11H)-one Hydrotrifluoroacetate The title compound was prepared according to the procedure in Example 5B except using (R,S)-8-methyl-7-[1-[[ [[(S)1-[(1,1-dimethylethoxy)carbonyl]-2-pyrrolidinylcarbonyl]amino]acetyl]oxy]propyl]indolizino [1,2-b]-quinolin-9(11H)-one. Anal. Calcd for $C_{26}H_{28}N_4O_4 \cdot 3/2\ CF_3CO_2H \cdot H_2O$: C, 53.62; H, 4.89; N, 8.63. Found: C, 53.64; H, 5.29; N, 8.50.

EXAMPLE 12

(±)-8-Methyl-7-[1-[[(dimethylamino)acetyl]oxy] propl]indolizino[1,2-b]quinolin-9(11H)-one Hydrochloride 12A. (±)-7-[1-[(Chloroacetyl)oxy]propyl]-8-methylindolizino[1,2-b]quinolin-9(11)-one To a suspension of (±)-7-(1-hydroxypropyl)-8-methylindolizino[1,2-b]quinolin-9(11H)-one (306 mg, 1.0 mmol) in freshly distilled CHCl$_3$ (45 mL) were added chloroacetic anhydride (205 mg, 1.2 mmol), pyridine (80 mL, 1.0 mmol) and 4-dimethylaminopyridine (12.2 mg, 0.1 mmol). The resulting mixture, which became homogeneous after 20 min, was allowed to stir at room temperature overnight. The mixture was concentrated under reduced pressure, and the residue was dissolved in CH$_2$Cl$_2$, washed successively with H$_2$O (2×), 0.1N NaOH and H$_2$O and dried over sodium sulfate. The solvent was removed in vacuo to afford the title compound. $^1$H NMR (CDCl$_3$) d 8.35 (s, 1H), 8.24 (d, 1H), 7.93 (d, 1H), 7.85 (m, 1H), 7.65 (m, 1H), 7.33 (s, 1H), 5.99 (dd, 1H), 5.28 (s, 2H), 4.19 (s, 2H), 2.40 (s, 3H), 2.12–1.95 (m, 2H), 1.00 (t, 3H). Anal. Calcd for $C_{21}H_{19}ClN_2O_3 \cdot 1/2\ H_2O$: C, 64.37; H, 5.14; N, 7.15. Found: C, 64.29; H, 4.86; N, 6.82.

12B. (±)-7-[1-[(Iodoacetyl)oxy]propyl]-8-methylindolizino [1,2-b]quinolin-9(11H)-one To a mixture of (±)-7-[1-[(chloroacetyl)oxy]propyl]-8-methylindolizino[1,2-b]quinolin-9(11H)-one (100 mg, 0.26 mmol) in acetone (10 mL) was added sodium iodide (150 mg, 1.0 mmol), and the resulting solution was heated at reflux for 1 h. Upon cooling, a solid precipitate appeared. The solvent was removed in vacuo, and the residue was partitioned between CH$_2$Cl$_2$ and H$_2$O. The organic extract was washed with H$_2$O (3×), dried over sodium sulfate and concentrated under reduced pressure to afford the title compound. $^1$H NMR (CDCl$_3$) d 8.35 (s, 1H), 8.22 (d, J=8.2 Hz, 1H), 7.92 (d, J=8.0 Hz, 1H), 7.81 (m, 1H), 7.66 (m, 1H), 7.38 (s, 1H), 5.91 (dd, J=7.9, 6.0 Hz, 1H), 5.26 (two s, 2H), 3.84 (d, J=10.1 Hz, 1H), 3.75 (d, J=10.1 Hz, 1H), 2.36 (s, 3H), 2.10–1.83 (m, 2H), 1.03 (t, J=7.4 Hz, 3H). Anal. Calcd for $C_{21}H_{19}IN_2O_3 \cdot 1/2\ H_2O$: C, 52.19; H, 4.17; N, 5.80. Found: C, 52.16; H, 4.05; N, 5.39.

12C. (±)-8-Methyl-7-[1-[[(dimethylamino)acetyl]oxy] propyl]indolizino[1,2-b]quinolin-9(11H)-one Hydrochloride A stream of dimethylamine was introduced into a solution containing (±)-7-[1-[(iodoacetyl)oxy]propyl]-8-methylindolizino[1,2-b]quinolin-9(11H)-one (50 mg, 0.11 mmol) in anhydrous CH$_2$Cl$_2$ (15 mL). The resulting solution was allowed to stir for 2 h and then was concentrated under reduced pressure. The residue was partitioned between CH$_2$Cl$_2$ and H$_2$O, and the organic layer was washed several times with H$_2$O and dried over sodium sulfate. Into this solution was bubbled a stream of HCl gas, and the resulting cloudy mixture was stirred for 15 min and then was concentrated in vacuo. The residue was dissolved in $H_2O$ and lyophilized to afford the title compound as an orange solid. $^1H$ NMR (DMSO-$d_6$) d 8.68 (s, 1H), 8.15 and 8.12 (two overlapping d, 2H), 7.86 (m, 1H), 7.71 (m, 1H), 7.17 (s, 1H), 5.96 (apparent br t, 1H), 5.26 (s, 2H), 4.41 (s, 2H), 2.84 (br s, 6H), 2.26 (s, 3H), 2.20–1.86 (m, 2H), 0.96 (t, J=7.3 Hz, 3H). CIMS ($NH_3$, m/e, rel. int.) 392 (100) [(M+H)$^+$]. Anal. Calcd for $C_{23}H_{25}N_3O_3$·2HCl·13/8$H_2O$: C, 55.96; H, 6.18; N, 8.51. Found: C, 56.27; H, 6.03; N, 8.04.

EXAMPLE 13

(±)-7-[1-[[(1,4'-Bipiperidin-1'-yl)acetyl]oxy]propyl]-8-methylindolizino[1,2-b]quinolin-9(11H)-one Hydroiodide To a suspension of (±)-7-[1-[(iodoacetyl)oxy]propyl]-8-methylindolizino[1,2-b]quinolin-9(11H)-one (50 mg, 0.11 mmol) in $CH_2Cl_2$ (4 mL) was added 4-piperidinopiperidine (17.6 mg, 0.11 mmol). After stirring at room temperature for 3.5 h, thin layer chromatographic analysis indicated that the reaction was incomplete,. Additional 4-piperidinopiperidine (2.7 mg, 0.016 mmol) was added, and stirring was continued for 2 d. The mixture was concentrated under reduced pressure, and the residue was purified by column chromatography eluting with a solvent gradient of 0–100% MeOH in $H_2O$ containing 1% HOAc. The title compound was obtained after lyophilization. $^1H$ NMR (CDCl$_3$) d 8.35 (s, 1H), 8.21 (d, J=8.4 Hz, 1H), 7.92 (d, J=8.3 Hz, 1H), 7.83 (m, 1H), 7.63 (m, 1H), 7.34 (s, 1H), 5.94 (apparent t, 1H), 5.26 (s, 2H), 3.32 (s, 2H), 3.00 (br m, 2H), 2.37 (s, 3H), 2.6–1.4 (m, 13H), 0.98 (t, J=7.4 Hz, 3H). Anal. Calcd for $C_{31}H_{38}N_4O_3$·1/4 HI·3/8 $H_2O$: C, 67.28; H, 7.10; N, 10.12. Found: C, 67.67; H, 6.79; N, 9.69.

EXAMPLE 14

(±)-8-Methyl-7-[1-[(4-morpholinylacetyl)oxy]propyl]indolizino[1,2-b]quinolin-9(11H)-one Hydrochloride The title compound was prepared according to the procedure in Example 13 except using (±)-7-[1-[(iodoacetyl)oxy]propyl]-8-methylindolizino[1,2-b]quinolin-9(11H)-one and morpholine. $^1H$ NMR (CDCl$_3$/MeOH-$d_4$) d 8.51 (s, 1H), 8.26 (d, J=8.5 Hz, 1H), 7.99 (d, J=8.3 Hz, 1H), 7.88 (m, 1H), 7.70 (m, 1H), 7.53 (s, 1H), 5.98 (dd, J=7.4, 5.9 Hz, 1H), 5.30 (s, 2H), 4.29 (s, 2H), 4.02 (br s, 4H), 3.45 (br s partially obscured by HOD peak), 2.33 (s, 3H), 2.10–1.87 (m, 2H), 1.03 (t, J=7.4 Hz, 3H). Anal. Calcd for $C_{25}H_{27}N_3O_4$·2HCl·$H_2O$: C, 57.25; H, 5.96; N, 8.01. Found: C, 57.37; H, 6.28; N, 7.65.

EXAMPLE 15

(±)-8-Methyl-7-[1-[[(4-methylpiperazin-1-yl)acetyl]oxy]propyl]indolizino[1,2-b]quinolin-9(11H)-one Hydrochloride The title compound was prepared according to the procedure in Example 13 except using (±)-7-[1-[(iodoacetyl)oxy]propyl]-8-methylindolizino[1,2-b]quinolin-9(11H)-one and N-methylpiperazine. $^1H$ NMR (DMSO-$d_6$) d 8.67 (s, 1H), 8.15 (m, 2H), 7.87 (m, 1H), 7.72 (m, 1H), 7.11 (s, 1H), 5.84 (m, 1H), 5.25 (s, 2H), 3.5–2.6 (m, 13H), 2.23 (s, 3H), 2.04–1.82 (m, 2H), 0.95 (t, J=7.5 Hz, 3H). Anal. Calcd for $C_{26}H_{30}N_4O_3$·2HCl·9/2 $H_2O$: C, 52.00; H, 6.88; N, 9.33. Found: C, 52.12; H, 9.11; N, 9.30.

EXAMPLE 16

(±)-7-[1-[[(1-Imidazolyl)acetyl]oxy]propyl]-8-methylindolizino[1,2-b]quinolin-9(11H)-one Hydrochloride The title compound was prepared according to the procedure in Example 13 except using (±)-7-[1-[(iodoacetyl)oxy]propyl]-8-methylindolizino[1,2-b]quinolin-9(11H)-one and imidazole. $^1H$ NMR (CDCl$_3$/MeOH-$d_4$) d 9.17 (s, 1H), 8.60 (s, 1H), 8.34 (d, 1H), 8.04 (d, 1H), 7.95 (m, 1H), 7.75 (m, 1H), 7.61 (s, 1H), 7.51 (br s, 1H), 7.41 (br s, 1H), 5.95 (m, 1H), 5.65 (d, 1H), 5.42 (d, 1H), 5.33 (s, 2H), 2.36 (s, 3H), 2.1–1.9 (m, 2H), 1.07 (t, 3H). Anal. Calcd for $C_{24}H_{22}N_4O_3$·2 HCl·11/4 $H_2O$: C, 53.68; H, 5.35; N, 10.43. Found: C, 53.52; H, 5.58; N, 10.29.

EXAMPLE 17

(±)-8-Methyl-7-[1-[(pyridinioacetyl)oxy]propyl] indolizino[1.2-b]quinolin-9(11H)-one iodide The title compound was prepared according to the procedure in Example 13 except using (±)-7-[1-[(iodoacetyl)oxy]propyl]-8-methylindolizino[1,2-b]quinolin-9(11H)-one and pyridine. $^1H$ NMR (CDCl$_3$/MeOH-$d_4$) d 9.09 (d, J=5.5 Hz, 2H), 8.65 (t, J=7.9 Hz, 1H), 8.51 (s, 1H), 8.17 (m, 3H), 7.99 (d, J=8.1 Hz, 1H). 7.89 (m, 1H), 7.70 (m, 1H), 7.50 (s, 1H), 6.05 (d, J=17.2 Hz, 1H), 6.02 (m, 1H).5.87 (d, J=17.2 Hz, 1H), 5.30 (s, 2H), 2.31 (s, 3H), 2.18–1.94 (m, 2H), 1.09 (t, J=7.4 Hz, 3H). Anal. Calcd for $C_{26}H_{24}IN_3O_3$·1/4 $H_2O$: C, 55.97; H, 4.43; N, 7.53. Found: C, 55.72; H, 4.30; N, 7.26.

EXAMPLE 18

(±)-7-[1-[[4-[(Dimethylamino)methyl]benzoyl]oxy]propyl[-8-methylindolizino[1,2-b]quinolin-9(11H)-one Hydrochloride 18A. (±)-7-[1-[[4(Chloromethyl)benzoyl]oxy]propyl]-8-methylindolizino[1,2-b]quinolin-9(11H)-one The title compound was prepared according to the procedure in Example 3A except using (±)-7-(1-hydroxypropyl)-8-methylindolizino[1,2-b]quinolin-9(11H)-one and 4-(chloromethyl)benzoic acid. $^1H$ NMR (CDCl$_3$) d 8.33 (s, 1H), 8.16 (m, 3H), 7.91 (br d, J=7.3 Hz, 1H), 7.78 (m, 1H), 7.61 (m, 1H), 7.51 (d, J=8.3 Hz, 2H), 7.40 (s, 1H), 6.11 (dd, J=8.1, 6.1 Hz, 1H), 5.26 (s, 2H), 4.63 (s, 2H), 2.45 (s, 3H), 2.21–1.93 (m, 2H), 1.08 (t, J=7.3 Hz, 3H). Anal. Calcd for $C_{27}H_{23}ClN_2O_3$·1/2 $H_2O$: C, 69.30; H, 5.17; N, 5.99. Found: C, 69.39; H, 5.16; N, 6.02.

18B. (±)-7-[1-[[4-[(Dimethylamino)methyl]benzoyl]oxy]propyl]-8-methylindolizino[1,2-b]quinolin-9(11H)-one Hydrochloride A suspension containing (±)-7-[1-[[4-(chloromethyl)benzoyl]oxy]propyl]-8-methylindolizino[1,2-b]quinolin-9(11H)-one (35 mg, 0.08 mmol) and sodium iodide (57 mg, 0.38 mmol) in dry acetone (50 mL) was heated at reflux for 1 h and then allowed to cool and stir at room temperature overnight. Into this mixture dimethylamine was bubbled for several min, and the mixture was allowed to stir at room temperature for 1 h. The mixture was concentrated under reduced pressure, and the residue was partitioned between $H_2O$ and $CH_2Cl_2$. The organic layer was washed with $H_2O$ and dried over sodium sulfate. The solvent was removed in vacuo, and the residue was purified by column chromatography eluting with a solvent gradient of 0–5% MeOH/ $CH_2Cl_2$. The isolated material was treated with 3 mL $H_2O$ and 0.3 mL 0.1N HCl and lyophilized to afford the title compound as a beige solid. $^1H$ NMR (CDCl$_3$/MeOH-$d_4$) d 8.44 (s, 1H), 8.26 (d, J=8.3 Hz, 2H), 8.17 (d, J=8.6 Hz, 1H), 7.96 (d, J=8.4 Hz, 1H), 7.82 (m, 1H), 7.74 (d, J=8.4 Hz, 2H), 7.66 (m, 1H), 7.55 (s, 1H), 6.14 (dd, J=7.9, 5.8 Hz, 1H), 5.28 (s, 2H), 4.31 (s, 2H), 2.80 (s, 6H), 2.44 (s, 3H), 2.20–1.95 (m, 2H), 1.11 (t, J=7.4 Hz, 3H). Anal. Calcd for $C_{29}H_{29}N_3O_3 \cdot 3/2$ HCl$\cdot 7/2$ $H_2O$: C, 59.51; H, 6.46; N, 7.18. Found: C, 59.91; H, 6.85; N, 6.85.

EXAMPLE 19

(±)-8-Methyl-7-[[4-(pyridiniomethyl)benzoyl]oxy] propyl]indolizino[1,2-b]quinolin-9(11H)-one trifluoroacetate To a suspension of (±)-7-(1-hydroxypropyl)-8-methylindolizino[1,2-b]quinolin-9(11H)-one and (77 mg, 0.25 mmol) in pyridine (8 mL) under an argon atmosphere was added 4-(chloromethyl)benzoic acid (250 mg, 1.3 mmol). The resulting mixture was allowed to stir at room temperature for 2.5 d and then was concentrated under reduced pressure. The residue was partitioned between $H_2O$ and $CH_2Cl_2$, and the phases were separated. The aqueous phase was adjusted to pH 7.5 by the addition of 5% aqueous $NaHCO_3$ and re-extracted with $CH_2Cl_2$. The aqueous layer was concentrated under reduced pressure, and the residue was applied to a $RP_{18}$ column and eluted with a solvent gradient of $H_2O$ to MeOH. The material that was isolated was chromatographed two additional times on a $RP_{18}$ column, eluting with a solvent gradient of 0.1% TFA/$H_2O$ to 0.1% TFA/MeOH to afford, after lyophilization, the title compound. $^1$H NMR (CDCl$_3$/MeOH-d$_4$) d 9.07 (d, J=5.7 Hz, 2H), 8.46 (m, 1H), 8.39 (s, 1H), 8.23 (d, J=8.2 Hz, 2H), 8.16 (d, J=8.6 Hz, 1H), 8.05 (m, 2H), 7.93 (d, J=8.5 Hz, 1H), 7.81 (m, 1H), 7.65 (m, 1H), 7.59 (d, J=8.2 Hz, 2H), 7.49 (s, 1H), 6.13 (dd, J=7.8, 5.9 Hz, 1H), 6.00 (s, 2H), 5.27 (s, 2H), 2.42 (s, 3H), 2.2–2.0 (m, 2H), 1.08 (t, J=7.4 Hz, 3H). Anal. Calcd for $C_{34}H_{28}F_3N_3O_5 \cdot 5/2$ $CF_3CO_2H \cdot 5/2$ $H_2O$: C, 49.53; H, 3.78; N, 4.44. Found: C, 49.53; H, 3.31; N, 4.27.

EXAMPLE 20

(±)-7-[1-[[(Chloromethyl)hydroxyphosphinyl]oxy] propyl-8-methylindolizino[1,2-b]quinolin-9(11H)-one Triethylamine Salt To a suspension of (±)-7-(1-hydroxypropyl)-8-methylindolizino[1,2-b]quinolin-9(11H)-one (92 mg, 0.3 mmol) in $CH_2Cl_2$ (5 mL) under an argon atmosphere was added $Et_3N$ (42 mL, 0.3 mmol) followed by chloromethylphosphonic dichloride (31 mL, 0.3 mmol). The resulting mixture was allowed to stir at room temperature for 2.5 d, and then $Et_3N$ (42 mL) and MeOH (200 mL) were added and stirring was continued overnight. The mixture was concentrated under reduced pressure, and the residue was partitioned between $H_2O$ and $CH_2Cl_2$. The organic layer was washed with $H_2O$ (2×), and the combined aqueous extracts were lyophilized. The material that was obtained was applied to a $RP_{18}$ column, eluted with a solvent gradient of $H_2O$ to MeOH and lyophilized to afford the title compound. $^1$H NMR (CDCl$_3$) d 8.27 (br s, 1H), 8.13 (m, 1H), 7.9–7.5 (m, 4H), 5.60 (m, 1H), 5.19 (br s, 2H), 3.49 (br d, J=10.2 Hz, 2H), 3.05 (m, ~3H), 2.0–1.8 (m, 2H), 1.28 (t, J=7.3 Hz, ~5–6H)1.00 (t, J=7.2 Hz, 3H). Anal. Calcd for $C_{20}H_{20}ClN_2O_4P \cdot 1/2$ $C_6H_{15}N \cdot 7/4$ $H_2O$: C, 55.15; H, 6.24; N, 6.99. Found: C, 54.94; H, 5.81; N, 6.92.

EXAMPLE 21

(±)-7-[1-[(2-Cyanoethoxy)hydroxyphosphinyl)oxy] propyl]-8-methylindolizino[1,2-b]quinolin-9(11H)-one Sodium Salt (±)-7-(1-Hydroxypropyl)-8-methylindolizino[1,2-b] quinolin-9(11H)-one (153 mg, 0.50 mmol), 2-cyanoethyl phosphate (derived from 322 mg, 1.0 mmol of the barium salt by the procedure of Moffatt, J. G., *J. Am. Chem. Soc.* 1963, 85, 1118), and N,N'-dicyclohexylcarbodiimde (462 mg, 2.24 mmol) in dry pyridine (4.0 mL) were heated at 45° C. for 24 h with exclusion of moisture. Water and MeOH were added to the reaction, and the solvents were all stripped off in vacuo. Additional $H_2O$ and MeOH were added along with NaOAc (1.02 g), an insoluble solid was removed by filtration, and the solvents were stripped off again. The residue was applied as an aqueous solution to a reversed phase column of Partisil 40 ODS-3 and eluted with a gradient of 0–100% MeOH/$H_2O$ to give the title compound. $^1$H NMR (MeOH-d$_4$) d 8.58 (s, 1H), 8.19 (d, J=8.1 Hz, 1H), 8.05 (dd, J=8.1, 1.0 Hz, 1H), 7.86 (m, 1H), 7.71 (s, 1H), 7.68 (m, 1H), 5.54 (m, 1H), 5.29 (s, 2H), 3.98 (m, 2H), 2.65 (t, J=6.1 Hz, 2H), 2.36 (s, 3H), 2.07–1.88 (m, 2H), 1.10 (t, J=7.4 Hz, 3H). Anal. Calcd for $C_{22}H_{21}N_3NaO_5P \cdot 15/4$ $H_2O$: C, 49.96; H, 5.43; N, 7.94. Found: C, 49.95; H, 5.22; N, 7.63.

EXAMPLE 22

(±)-8-Methyl-7-[1-[(phosphono)oxy]propyl] indolizino[1,2-b]quinolin-9(11H)-one Trimethylamine Salt To (±)-7-[1-[(2-cyanoethoxy)hydroxyphosphinyl)oxy] propyl]-8-methylindolizino[1,2-b]quinolin-9(11H)-one sodium salt (89.4 mg, 0.19 mmol) in MeOH (1.0 mL) was added 1N NaOH (1.65 mL), and the reaction mixture was stirred under argon for 7 h at room temperature. The reaction was acidified with 1N HCl (1.75 mL), stripped and redissolved in $H_2O$. This solution was applied of a reversed phase column of Partisil 40 ODS-3 and eluted with a gradient of 0–100% MeOH/$H_2O$. After some of the title compound eluted as a sodium salt, another fraction came off as mostly the free acid. The acid fraction was dissolved in MeOH, and $(CH_3)_3N$ in MeOH was added to raise the pH to approximately 10. The MeOH was stripped off, $H_2O$ was added and the solution was lyophilized to give the title compound as a partial sodium salt. $^1$H NMR (MeOH-d$_4$/$D_2O$) d 8.58 (s, 1H), 8.16 (d, J=8.5 Hz, 1H), 8.04 (d, J=8.3 Hz, 1H), 7.85 (m, 1H), 7.74 (s, 1H), 7.68 (m, 1H), 5.50 (br dd, 1H), 5.26 (s, 2H), 2.92 (s, ~6.5H), 2.33 (s, 3H), 1.95 (m, 2H), 1.08 (t, J=7.4 Hz, 3H). Anal. Calcd for $C_{19}H_{18}N_2O_5P \cdot 3/4$ $C_3H_{10}N \cdot 1/4$ $Na \cdot 9/2$ $H_2O$: C, 49.35; H, 6.72; N, 7.45. Found: C, 49.41; H, 6.43; N, 7.02.

EXAMPLE 23

(±)-7-[1-[[(Aminomethyl)hydroxyphosphinyl]oxy] propyl]-8-methylindolizino[1,2-b]quinolin-9(11H)-one 23A. (±)-7-[1-[[[[(9-Fluorenylmethoxy)carbonyl]amino] methyl]hydroxyphosphinyl]oxy]propyl]-8-methylindolizino [1,2-b]quinolin-9(11H)-one The title compound was prepared according to the procedure in Example 21 except using (±)-7-(1-hydroxypropyl) -8-methylindolizino[1,2-b]quinolin-9(11H)-one and [[[(9-fluorenylmethoxy)carbonyl]amino]methyl]phosphonic acid. Anal. Calcd for $C_{35}H_{32}N_3O_6P \cdot 9/8$ $H_2O$: C, 65.49; H, 5.38; N, 6.55. Found: C, 65.83; H, 5.28; N, 6.14.

23B. (±)-7-[1-[[(Aminomethyl)hydroxyphosphinyl]oxy] propyl]-8-methylindolizino[1,2-b]quinolin-9(11H)-one A mixture of $Et_2NH$ (10 mL) and (±)-7-[1-[[[[(9-fluorenylmethoxy)carbonyl]amino]methyl] hydroxyphosphinyl]oxy]propyl]-8-methylindolizino[1,2-b] quinolin-9(11H)-one (328 mg, 0.51 mmol) was stirred at room temperature in a capped vial for 3 h. The reaction mixture was stripped to dryness, and H$_2$O was added. The this partial solution was extracted with EtOAc, filtered and lyophilized to give a viscous oil which was triturated with CH$_3$CN to produce a golden solid. The solid was dissolved in H$_2$O and lyophilized to give the title compound as a partial Et$_2$NH salt. $^1$H NMR (CDCl$_3$/MeOH-d$_4$) d 8.49 (s, 1H), 8.12 (d, J=8.7 Hz, 1H), 8.00 (d, J=8.3 Hz, 1H), 7.84 (m, 1H), 7.69 (overlapping s and m, 2H), 5.59 (dd, J=14.9, 6.5 Hz, 1H), 5.27 (s, 2H), 2.98 (q, J=7.2 Hz, ~1.1H), 2.85 (dd, J=12.7, 2.6 Hz, 2H), 2.31 (s, 3H), 2.02–1.83 (m, 2H), 1.31 (t, I=7.3 Hz, ~1.8H), 1.05 (t, J=7.4 Hz, 3H). Anal. Calcd for C$_{20}$H$_{22}$N$_3$O$_4$P.1/4 C$_4$H$_{11}$N.5 H$_2$O: C, 49.68; H, 6.90; N, 8.97. Found: C, 50.08; H, 6.49; N, 8.46.

EXAMPLE 24

12-[[(Aminoacetyl)oxy]methyl]-8-methyl-7-(1-oxopropyl)indolizino[1,2-b]quinolin-9(11H)-one Hydrofluoroacetate 24A. 8-Methyl-12-[[[[[(1,1-dimethylethoxy)carbonyl]amino]acetyl]oxy]methyl]-7-(1-oxopropyl)indolizino[1,2-b]quinolin-9(11)-one The title compound was prepared according to the procedure in Example 5E except using 12-(hydroxymethyl)-8-methyl-7-(1-oxopropyl)indolizino[1,2-b]quinolin-9(11H)-one and N-[(1,1-dimethylethoxy)carbonyl]glycine.

24B. 12-[[(Aminoacetyl)oxy]methyl]-8-methyl-7-(1-oxopropyl)indolizino[1,2-b]quinolin-9(11H)-one Hydrotrifluoroacetate The title compound was prepared according to the procedure in Example 5B except using 8-methyl-12-[[[[[(1,1-dimethylethoxy)carbonyl]amino]acetyl]oxy]methyl]-7-(1-oxopropyl)indolizino[1,2-b]quinolin-9(11H)-one. $^1$H NMR (D$_2$O/DSS) d 7.6–7.3 (m, 4H), 6.64 (s, 1H), 5.58 (s, 2H), 4.58 (s, 2H), 4.20 (s, 2H), 2.92 (q, J=7.2 Hz, 2H), 1.94 (s, 3H), 1.22 (t, J=7.2 Hz, 3H). Anal. Calcd for C$_{22}$H$_{21}$N$_3$O$_4$.CF$_3$CO$_2$H.H$_2$O: C, 55.07; H, 4.62; N, 8.03. Found: C, 55.32; H, 4.69; N, 7.98.

EXAMPLE 25

8-Methyl-12-[[(4-morpholinoacetyl)oxy]methyl]-7-(1-oxopropyl)indolizino[1,2-b]quinolin-9(11H)-one Hydrochloride To a suspension of 12-hydroxymethyl-8-methyl-7-(1-oxopropyl)indolizino[1,2-b]quinolin-9(11H)-one (523 mg, 1.56 mmol) in anhydrous CH$_2$Cl$_2$ (58 mL) at room temperature under an argon atmosphere was added anhydrous pyridine (130 µL, 1.61 mmol) and 4-dimethylaminopyridine (19 mg, 0.16 mmol). The reaction was stirred for 10 min and then was treated with iodoacetic anhydride (554 mg, 1.57 mmol) in one portion. After 1 h the turbid orange solution was treated with morpholine (815 µL, 9.4 mmol) and stirred for 1 h. The reaction mixture was filtered to remove morpholine hydroiodide, and the filtrate was concentrated in vacuo at 15° C. and purified by flash chromatography eluting with 2% MeOH in CHCl$_3$ to give, after removal of solvent, a yellow powder which was suspended in H$_2$O (10 mL) and treated with 0.1N HCl (16 mL) to give a pH of 1.7. The resulting slurry was filtered and washed with MeCN followed by Et$_2$O to give the title compound as yellow flakes(, mp. 148°–150° C. (dec.). $^1$H NMR (CDCl$_3$) d 8.22 (d, J=8.6 Hz, 1H), 8.11 (d, J=8.6 Hz, 1H), 7.84 (m, 1H), 7.70 (m, 1H), 7.25 (s, 1H), 5.77 (s, 2H), 5.50 (s, 2H), 3.73 (m, 4H), 3.33 (s, 2H), 2.92 (q, J=7.6 Hz, 2H), 2.58 (m, 4H), 2.31 (s, 3H), 1.26 (t, J=7.6 Hz, 3H). Anal. Calcd for C$_{26}$H$_{27}$N$_3$O$_5$.HCl.1/2 H$_2$O: C, 61.60; H, 5.77; N, 8.29. Found: C, 61.62; H, 5.94; N, 8.25.

EXAMPLE 26

8-[[(Dimethylaminoacetyl)oxy]methyl]-7-(1-oxopropyl)indolizino[1,2-b]quinolin-9(11H)-one Hydrochloride 26A. 8-[[(Iodoacetyl)oxy]methyl]-7-(1-oxopropyl)indolizino[1,2-b]quinolin-9(11H)-one To a suspension of (±)-3-ethyl-1,11-dihydro-3-hydroxy-3H,13H-furo[3',4':6,7]indolizino[1,2-b]quinolin-13-one (320 mg, 1.00 mmol) in dry CH$_2$Cl$_2$ (20 mL) under argon was added over 4 min diisobutylaluminum hydride (1.10 mL of 1.0M in CH$_2$Cl$_2$). After 15 min iodoacetic anhydride (530 mg, 1.50 mmol) was added in one portion. After 2 h, MeOH (10 mL) was added to the reaction, and after stirring 20 min, the solvent was removed in vacuo. The residue was dissolved in CH$_2$Cl$_2$ and chromatographed on silica gel eluting with a gradient of 0–5% MeOH/CH$_2$Cl$_2$ to give the title compound and some unreacted starting material. $^1$H NMR (CDCl$_3$) d 8.42 (s, 1H), 8.24 (d, J=8.4 Hz, 1H), 7.96 (d, J=8.3 Hz, 1H), 7.85 (m, 1H), 7.69 (m, 1H), 7.29 (s, 1H), 5.33 (s, 4H), 3.70 (s, 2H), 2.99 (q, J=7.2 Hz, 2H), 1.28 (t, J=7.2 Hz, 3H). CIMS (NH$_3$, m/e, rel. int.) 489 (100) [(M+H)$^+$]. Anal. Calcd for C$_{21}$H$_{17}$IN$_2$O$_4$.1/2 H$_2$O: C, 50.72; H, 3.65; N, 5.63. Found: C, 50.53; H, 3.35; N, 5.45.

26B. 8-[[(Dimethylaminoacetyl)oxy]methyl]-7-(1-oxopropyl)indolizino[1,2-b]quinolin-9(11H)-one Hydrochloride A suspension of 8-[[(iodoacetyl)oxy]methyl]-7-(1-oxopropyl)indolizino[1,2-b]quinolin-9(11H)-one (48.8 mg, 0.098 mmol) in dry CH$_2$Cl$_2$ (5.0 mL) was covered by an atmosphere of (CH3)$_2$NH (balloon). Within a few min the solid had dissolved and after 5 min the reaction was stripped to dryness. The residue was dissolved in CH$_2$Cl$_2$, washed first with 5% aqueous NaHCO$_3$ and then with H$_2$O, and dried over Na$_2$SO$_4$. The solvent was removed in vacuo, and the residue was suspended in H$_2$O (20 mL) to which was added 1N HCl (100 µL) to dissolve most of the solid. After filtration, lyophilization gave the title compound. $^1$H NMR (CDCl$_3$/MeOH-d$_4$) d 8.47 (s, 1H), 8.23 (d, J=8.3 Hz, 1H), 7.98 (d, J=7.5 Hz, 1H), 7.87 (m, 1H), 7.71 (m, 1H), 7.44 (s, 1H), 5.38 (s, 2H), 5.35 (s, 2H), 3.95 (s, 2H), 3.05 (s, 6H), 3.02 (q, J=7.1 Hz, 2H), 1.27 (t, J=7.1 Hz, 3H). Anal. Calcd for C$_{23}$H$_{23}$N$_3$O$_4$.HCl.7/4 H$_2$O: C, 58.35; H, 5.86; N, 8.88. Found: C, 58.26; H, 5.51; N, 8.68.

EXAMPLE 27

8-[[(4-Morpholinoacetyl)oxy]methyl]-7-(1-oxopropyl)indolizino[1,2-b]quinolin- 9(11H)-one Hydrochloride A suspension of 8-[[(iodoacetyl)oxy]methyl]-7-(1-oxopropyl)indolizino[1,2-b]quinolin-9(11H)-one (138.2 mg, 0.278 mmol) in dry CH$_2$Cl$_2$ (18 mL) containing morpholine (75 µL, 0.86 mmol) was stirred with moisture exclusion for 1.5 h, and then H$_2$O was added and the layers separated. The organic layer was washed successively with H$_2$O, 5% aqueous NaHCO$_3$, and finally H$_2$O. After drying over Na$_2$SO$_4$, the organic layer was stripped to dryness, and H$_2$O (50 mL) and 1N HCl (284 µL) were added to dissolve all the residue. Lyophilization gave the title compound. $^1$H NMR (CDCl$_3$/MeOH-d$_4$) d 8.50 (s, 1H), 8.23 (d, J=8.6 Hz, 1H), 8.00 (d, J=8.1 Hz, 1H), 7.88 (m, 1H), 7.72 (m, 1H), 7.47 (s, 1H), 5.37 (s, 2H), 5.35 (s, 2H), 4.08 (br s, 4H), 3.99 (s, 2H), 3.50 (br s, 4H), 3.05 (s, 6H), 3.03 (q, J=7.1 Hz, 2H), 1.28 (t, J=7.2 Hz, 3H). Anal. Calcd for C$_{25}$H$_{25}$N$_3$O$_5$.5/4HCl.7/4 H$_2$O: C, 57.24; H, 5.72; N, 8.01. Found: C, 57.17; H, 5.33; N, 7.62.

We claim:

1. A compound of Formula I, or a pharmaceutically acceptable salt thereof

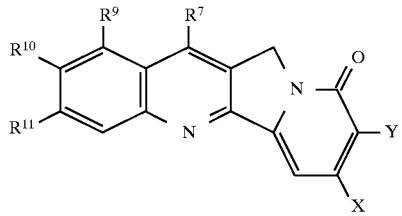

wherein:

R⁷ is —H, —CN, lower alkyl, —(CH₂)ₙCH₂V where n=0–3;

R⁹ is —H, —OR, —NRR¹, —CN, —(CH₂)ₙCH₂V where n=0–3;

R¹⁰ is —H, —OR, —NRR¹, —CN, —COR¹², —CH(OH)R¹², —O—(CH₂)₁₋₅CH₂NRR¹, —OC(O)NRR¹, 1,4'-bipiperidine-1'-carboxy, —(CH₂)ₙCH₂V where n=0–3;

V is —OH, —OCOR¹⁴, —OP(O)(OH)R¹⁵, or —NRR¹;

R¹¹ is —H, or —OR;

R¹² is —H or lower alkyl;

R and R¹ are independently selected from the group consisting of —H,

—C₁₋₆ alkyl, and, when R and R¹ are substituted on nitrogen, R and R¹ can be taken together to form a 5–7 membered saturated heterocyclic ring containing the nitrogen;

R¹⁴ is —CR¹²R¹⁶R¹⁷,

—(CH₂)ₙCH₂R¹⁷ (where n=1–3);

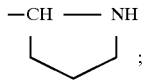

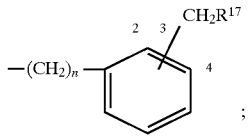

(where n=0 or 1, and CH₂R¹⁷ can be substituted on the phenyl at the 2, 3, or 4 position);

—O(CH₂)ₙCH₂R¹⁷ (where n=1–3);

—NRR¹;

—NH(CH₂)ₙCH₂R¹⁷ (where n=1–3);

R¹⁵ is OH, OR¹⁸, or CH₂NH₂;

R¹⁶ is H or the side chain of any naturally occurring α-amino acid; R¹⁷ is NRR¹,

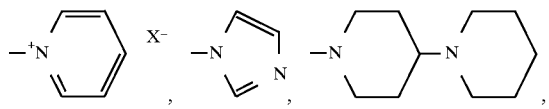

where X is any pharmaceutically acceptable anion;

R¹⁸ is lower alkyl;

X is —CHR³R⁴ or

Y is —CH₃, or —CH₂OR²;

R² is —H, —C(O)H, —COR¹⁴, or —P(O)(OH)R¹⁵;

R³ is —OH, —OCOR¹⁴, or —OP(O)(OH)R¹⁵;

R4 is —H, lower alkyl, or —OR; and

R⁶ is —H or lower alkyl;

provided that:

a) if one of R⁷, R⁹, R¹⁰ or R¹¹ is other than —H, only one of the others may be other than —H;

b) only one of R⁹ or R¹⁰ may be —NRR¹;

c) when X is —CHR³R⁴ and R⁴ is —OR, R³ is —OH;

d) when Y is —CH₂OR², X is

e) when R⁷, R⁹, R¹⁰, and R¹¹ are all —H and Y is —CH₃, then X is not —C(O)H, —CH₂OH, or —C(O)CH₂CH₃;

f) when R⁷, R⁹, R¹⁰ and R¹¹ are all —H and Y is —CH₂OC(O)H, then X is not —C(O)CH₂CH₃, and g) when R⁷, R⁹, R¹⁰, R¹¹ are all —H, Y is —CH₃, X is —CHR³R⁴, and R³ is —OH; then R⁴ is not lower alkyl.

2. A compound of claim 1 wherein: R⁷, R⁹, R¹⁰, and R¹¹ are each —H; X is —CHR³R⁴ where R⁴ is —H, or X is

where R⁶ is —H or lower alkyl; and Y is —CH₃ or CH₂OR².

3. A compound of claim 2 wherein said compound is 7-[1-[(aminoacetyl)oxy]propyl]-8-methylindolizino[1,2-b]quinolin-9(11H)-one.

4. A compound of claim 2 wherein said compound is 7-[1-[(3-amino-1-oxopropyl)oxy]propyl]-8-methylindolizino[1,2-b]quinolin-9(11H)-one.

5. A compound of claim 2 wherein said compound is 8-methyl-7-[1-[(-2-pyrrolidinylcarbonyl)oxy]propyl]indolizino[1,2-b]quinolin-9(11H)-one.

6. A compound of claim 2 wherein said compound is 7-[1-[(2-amino-2-methyl-1-oxopropyl)oxy]propyl]-8-methylindolizino[1,2-b]quinolin-9(11H)-one.

7. A compound of claim 2 wherein said compound is 8-methyl-7-[1-[[(2-pyrrolidinylcarbonyl)aminoacetyl]oxy]propyl]indolizino[1,2-b]quinolin-9(11H)-one.

8. A compound of claim 2 wherein said compound is 8-methyl-7-[1-[(4-morpholinylacetyl)oxy]propyl]indolizino[1,2-b]quinolin-9(11H)-one.

9. A compound of claim 2 wherein said compound is 8-methyl-7-[1-[(pyridinioacetyl)oxy]propyl]indolizino[1,2-b]quinolin-9(11H)-one iodide.

10. A compound of claim 2 wherein said compound is 7-[1-[[4-[(dimethylamino)methyl]benzoyl]oxy]propyl]-8-methylindolizino[1,2-b]quinolin-9(11H)-one.

11. A compound of claim 2 wherein said compound is 8-methyl-7-[1-[(phosphono)oxy]propyl]indolizino[1,2-b]quinolin-9(11H)-one.

12. A compound of claim 2 wherein said compound is 7-[1-[[(aminomethyl)hydroxyphosphinyl]oxy]propyl]-8-methylindolizino[1,2-b]quinolin-9(11H)-one.

13. A compound of claim 1 wherein: X is

an Y is $CH_2OR^2$.

14. A compound of claim 13 wherein said compound is 8-[[(4-morpholinoacetyl)oxy]methyl]-7-(1-oxopropyl)indolizino[1,2-b]quinolin-9(11H)-one.

15. A compound of claim 1 wherein: $R^7$ is $(CH_2)_nCH_2V$, where n=0 and V is —OH; X is

and Y is —$CH_3$.

16. A compound of claim 15 wherein said compound is 8-methyl-12-[[(4-morpholinoacetyl)oxy]methyl]-7-(1-oxopropyl)indolizino[1,2-b]quinolin-9(11H)-one hydrochloride.

17. A compound of claim 1 wherein: $R^7$, $R^9$, and $R^{11}$ are each —H; provided that $R^{10}$ is not —H.

18. A compound of claim 17 wherein: $R^{10}$ is —OR, —CN, —$COR^{12}$, or —$(CH_2)_nCH_2V$; X is —$CHR^3R^4$ where $R^4$ is —H or lower alkyl, or X is

19. A compound of claim 18 wherein said compound is 7-[1-[(aminoacetyl)oxy]propyl]-2-cyano-8methylindolizino[1,2-b]quinolin-9(11H)-one.

20. A compound of claim 18 wherein: $R^{10}$ is —$(CH_2)_n CH_2V$; and X is

$R^6$ is $CH_2CH_3$.

21. A compound of claim 1 wherein: $R^7$ and $R^{11}$ are each —H; provided that $R^9$ and $R^{10}$ are each not —H.

22. A compound of claim 21 wherein: $R^9$ is —$(CH_2)_nCH_2V$; $R^{10}$ is —OR; X is —$CHR^3R^4$ where $R^4$ is —H or lower alkyl, or X is

and Y is —$CH_3$ or $CH_2OR^2$.

23. A compound of claim 1 wherein: $R^9$, $R^{10}$, and $R^{11}$ are each —H; provided that $R^7$ is not —H.

24. A compound of claim 23 where $R^7$ is lower alkyl, —CN, or —$(CH_2)_nCH_2V$; X is —$CHR^3R^4$ where $R^4$ is —H or lower alkyl, or X is

25. A compound of claim 24 wherein said compound 7-[1-[(aminoacetyl)oxy]propyl]-12-cyano-8-methylindolizino[1,2-b]quinolin-9(11H)-one.

26. A compound of claim 1 wherein: $R^7$, $R^{10}$, and $R^{11}$ are each —H; provided that $R^9$ is not —H.

27. A compound of claim 26 wherein: $R^9$ is —OR, X is —$CHR^3R^4$ where $R^4$ is —H or lower alkyl.

28. A compound of claim 1 wherein: $R^7$, $R^9$, and $R^{10}$ are each —H; provided that $R^{11}$ is not —H.

* * * * *